(12) United States Patent
Cederlund

(10) Patent No.: US 11,004,545 B2
(45) Date of Patent: May 11, 2021

(54) CLINICAL EFFECT OF PHARMACEUTICAL PRODUCTS USING COMMUNICATION TOOL INTEGRATED WITH COMPOUND OF SEVERAL PHARMACEUTICAL PRODUCTS

(71) Applicant: Intellectual Property Enabler Stockholm AB, Bromma (SE)

(72) Inventor: Johan Cederlund, Bromma (SE)

(73) Assignee: INTELLECTUAL PROPERTY ENABLER STOCKHOLM AB, Bromma (SE)

( * ) Notice: Subject to any disclaimer, the term of this patent is extended or adjusted under 35 U.S.C. 154(b) by 0 days.

(21) Appl. No.: 16/160,519

(22) Filed: Oct. 15, 2018

(65) Prior Publication Data
US 2019/0122749 A1    Apr. 25, 2019

Related U.S. Application Data

(63) Continuation of application No. 14/417,265, filed as application No. PCT/SE2013/050896 on Jul. 12, 2013, now abandoned.

(30) Foreign Application Priority Data

Jul. 24, 2012 (SE) .............................. SE1250893-3

(51) Int. Cl.
*G16H 10/20* (2018.01)
*G16H 20/10* (2018.01)
(Continued)

(52) U.S. Cl.
CPC ............. *G16H 10/20* (2018.01); *G06F 19/00* (2013.01); *G16H 20/10* (2018.01); *G16H 70/40* (2018.01); *G16Z 99/00* (2019.02); *G06Q 50/22* (2013.01)

(58) Field of Classification Search
CPC ......... G16H 10/20; G16Z 99/00; G06F 19/00; G06Q 50/22
See application file for complete search history.

(56) References Cited

U.S. PATENT DOCUMENTS 5,572,421 A    11/1996  Altman
5,633,910 A    5/1997   Cohen
(Continued)

FOREIGN PATENT DOCUMENTS

JP    2006-252305    9/2006
WO    WO 2008/057606    5/2008
(Continued)

OTHER PUBLICATIONS

International Search Report, dated Jan. 17, 2014, from corresponding PCT application.
(Continued)

*Primary Examiner* — Eliza A Lam
(74) *Attorney, Agent, or Firm* — Nixon & Vanderhye

(57) ABSTRACT

A combination of N>1 substances with pharmaceutical activity against at least one medical condition for treating the medical condition with a program including instructions causing a computer to perform a method including:
providing a patient with a set of questions adapted to the combination according to a question schedule;
providing a patient with N sets of questions according to N question schedules, wherein each set of questions is adapted to one substance;
collecting answers to the sets of questions from the patient;
subjecting the answers to the set of questions adapted to the combination to a set of functions, thereby generating a first patient feedback;
(Continued)

subjecting the answers to the sets of questions each adapted for one substance, to N sets of functions, thereby generating a second patient specific feedback; and providing the first and second specific feedbacks to the patient.

19 Claims, 10 Drawing Sheets

(51) Int. Cl.
    *G16H 70/40*     (2018.01)
    *G16Z 99/00*     (2019.01)
    *G06F 19/00*     (2018.01)
    *G06Q 50/22*     (2018.01)

(56) References Cited

U.S. PATENT DOCUMENTS

| | | |
|---|---|---|
| 7,251,609 B1 | 7/2007 | Mcalindon et al. |
| 8,540,516 B2 | 9/2013 | Williams |
| 2001/0034639 A1 | 10/2001 | Jacoby et al. |
| 2002/0035486 A1 | 3/2002 | Huyn |
| 2002/0099570 A1 | 7/2002 | Knight |
| 2002/0192159 A1 | 12/2002 | Reitberg |
| 2003/0036683 A1* | 2/2003 | Kehr .................. G06F 19/325 600/300 |
| 2003/0036923 A1 | 2/2003 | Waldon et al. |
| 2009/0131758 A1 | 5/2009 | Heywood et al. |
| 2010/0023346 A1 | 1/2010 | Paty et al. |
| 2011/0209065 A1 | 8/2011 | Del Rio et al. |
| 2011/0288887 A1 | 11/2011 | Duke et al. |
| 2012/0030231 A1 | 2/2012 | Copper |
| 2012/0036103 A1 | 2/2012 | Stupp et al. |

FOREIGN PATENT DOCUMENTS

| | | | | |
|---|---|---|---|---|
| WO | WO-2008057606 A2 * | 5/2008 | ......... | G06F 19/3456 |
| WO | WO-2009063209 A1 * | 5/2009 | ............. | G16H 10/20 |

OTHER PUBLICATIONS

Jul. 25, 2017, JP communication issued for related JP Application No. 2015-524225.

* cited by examiner

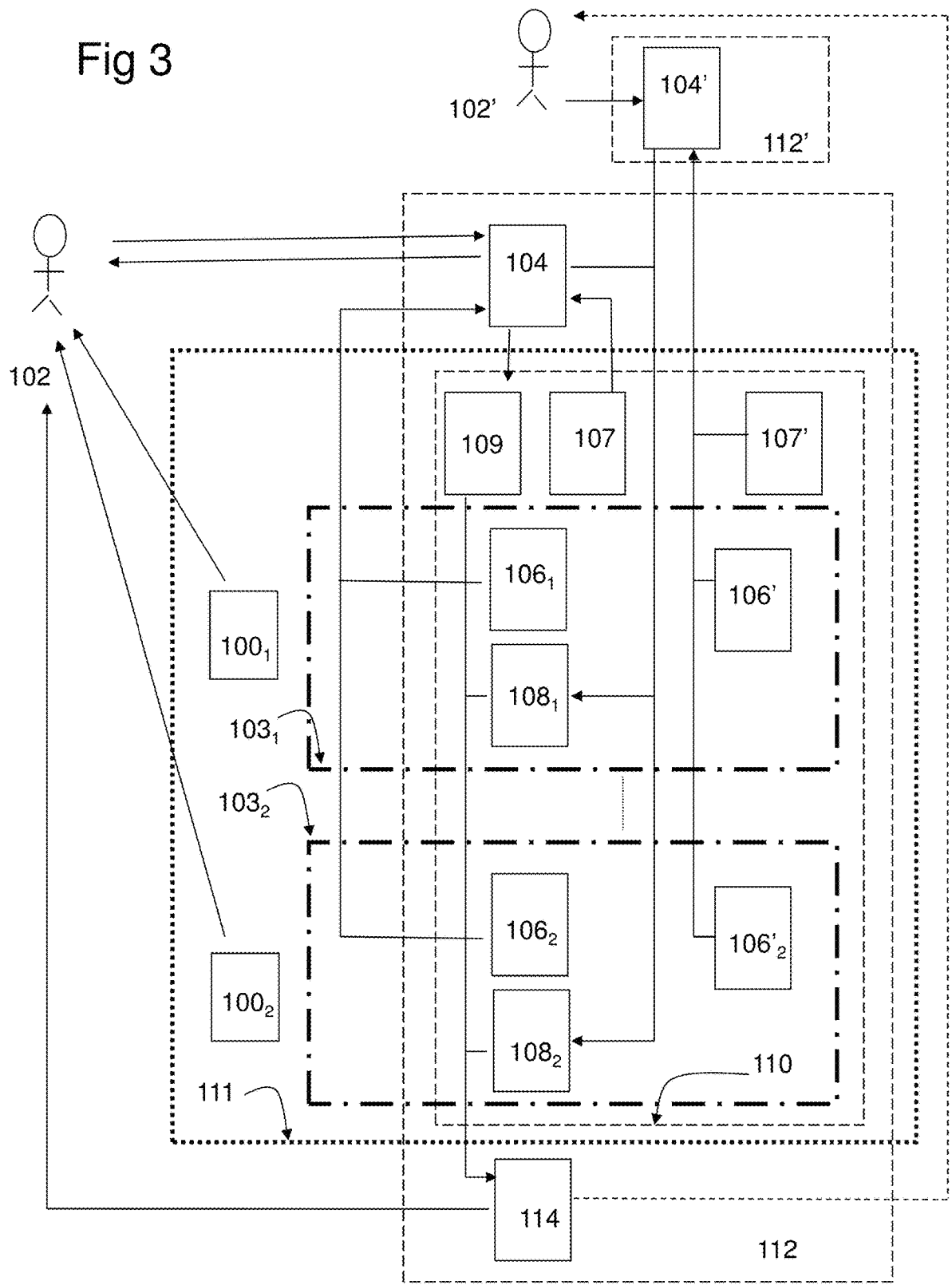

CLINICAL EFFECT OF PHARMACEUTICAL PRODUCTS USING COMMUNICATION TOOL INTEGRATED WITH COMPOUND OF SEVERAL PHARMACEUTICAL PRODUCTS

FIELD OF THE INVENTION

The present invention relates to the field of improving the usage and clinical efficacy of pharmaceutical products in clinical practice, improving health situation of patients, where a combination of pharmaceutical products is one component in the combined product and a computer application is another.

BACKGROUND

Today pharmaceutical products on the market are powerful products solving health problems of the patients. However, most often they solve just a specific problem or symptom of the patient, i.e. a limited part of the patient needs; meanwhile the patient experiences a wider complex situation with several other issues and symptoms due to their illness. There is a need for a broader and more profound solution for a significant number of patients. This is especially the case for several therapy areas such as the cardiovascular, the diabetes, the chronic pain, the oncology, the respiratory and the CNS areas and in particular for patients with multiple diagnoses.

Today a lot of patients, especially the elderly with multiple and severe diagnoses, have several different drugs where each drug should address one or a few of the patient's symptoms. The possibility to evaluate if the drugs are clinically efficient, as well as optimized for the circumstances of the patient, and especially not causing any safety concerns, are in most cases missing. A lot of drugs interact with each other often causing negative health effects for the patients and sometimes critical situations. Today a lot of patients are forced to emergency healthcare visits due to unsuitable medication.

Today drugs on the market are thoroughly tested with regard to their clinical affect and safety during extensive clinical trials before they are approved for marketing by a national or regional Medical Products Agency, such as EMA in Europe or FDA in the U.S. In most cases, however, there are no verifications, or clinical trials, evaluating the situation of the patients in real clinical practice concerning the situation that several patients are taking a mix of multiple pharmaceuticals.

For several diagnoses, according to existing guidelines, a patient should be prescribed multiple separate pharmaceutical products in order to solve the complete health problems of the patient. Patients with, for example, Acute Coronary Syndrome should be prescribed approximately six different pharmaceutical drugs.

The existing knowledge of drugs that have been on the market for some time is mostly very well-known due to the performed clinical trials and the period of utilization of the drugs in clinical practice. This information is often available for several different actors to utilize for researching purposes, but not effectively available directly to the individual patient using the drug.

Today drugs in clinical practice are not possible to individualize to the circumstances of each specific patient. Instead estimation is done by the physician each time a drug is prescribed to a patient based upon his/her knowledge and the presented data from earlier performed clinical trials for a specific drug. There is seldom any follow-up of the results of the specific patient in clinical practice, and if the patient not themselves responds in any way to the results of the medication, no action is done to improve or secure the result of the treatment.

Drugs on the market today are stand-alone products without any support or connection to the vast amount of data generated during the research and development phase of the product, as well as the information gathered during clinical practice, which could be used for simplifying and optimizing the relation between the patient needs and the pharmaceutical product clinical conditions. The guidance for matching patient specific conditions to the use of pharmaceutical products is limited. The support for finding an optimal dosage for a specific patient is also missing.

One of the major issues to reach an increased clinical effect of pharmaceutical treatments in clinical practice is to improve adherence to prescribed medication, see World Health Organisation 2003 Report: Adherence to long-term therapies; Evidence for action: (available at http://whqlibdoc.who.int/publications/2003/9241545992.pdf)

Due to the lack of adherence to medication the results of pharmaceutical treatments in clinical practice have difficulties in reaching similar results of clinical effect as the ones made in clinical trials during the development of the pharmaceutical products.

In regulations from FDA and EMA focus on patient safety and follow-up of side effects, as well as possible adverse events, regarding pharmaceuticals is crucial. In clinical practice, however, this is difficult to achieve and the patient is mainly responsible with little or no support to accomplish it properly.

Even though the safety concerns of medications are directly related to the specific pharmaceutical products, today there are very limited features, or no features, at all integrated with the pharmaceutical product aiming at improving the patient safety concerns of the product. It is up to the patients themselves to handle the safety issues.

Medical devices enhancing the therapeutic effect of drugs are known. For instance, specifically designed inhalers are used to administer various anti-asthmatic drugs and implantable devices have been used for controlled release of anticancer drugs.

Patient compliance and monitoring systems are known in the art, e.g. WO02095352. Such systems are focused on monitoring patient compliance and reporting to the medical practitioner and the patient how the treatment is progressing. The system disclosed in WO02095352 is relevant for a certain condition (menopause) and a general therapy (hormone replacement therapy). It is not specifically adapted for a particular pharmaceutical product.

Different types of e-health applications are existing knowledge, as well as, the positive clinical effects of such systems. This kind of applications is focused on improving the health situation for the patient in general independent of any specific pharmaceutical. This kind of system has a large interest within clinical practice, but the broad usage of such systems today within healthcare is absent.

SUMMARY OF THE INVENTION

A central aspect of the invention is a combination product where a computer program product is integrated with two or more included pharmaceutical products through a connected question-analysis-feedback model (QAFM). A physician will be able to prescribe the combination product, with the following included components; the computer program product, the QAFM and the pharmaceutical products, to patients.

This aspect of the invention can be described as a combination of N substances, wherein N>1, with pharmaceutical activity against at least one medical condition for use in a treatment of said at least one medical condition in combination with a computer program product (110) comprising instructions causing a computer to perform a method comprising the steps providing a patient (102) with a set of questions (107) according to a question schedule, wherein said set of questions is adapted to said combination of substances;

providing a patient with N sets of questions ($106_1$-$106_N$) according to N question schedules, wherein each set of questions is adapted to one of the substances in said combination;

collecting answers to said sets of questions from said patient;

subjecting the answers to said set of questions (107) adapted to said combination of substances to a set of functions (109), thereby generating a first patient specific feedback information;

subjecting the answers to said sets of questions ($106_1$,-$106_N$), each adapted for one of the substances in said combination, to n sets of functions ($108_1$,-$108_N$), thereby generating a second patient specific feedback information;

providing said first and second patient specific feedback to the patient; and optionally extracting information from said answers and providing said information to a database adapted for collecting information during clinical use of said combination of substances.

Preferred embodiments of this aspect are detailed in the dependent claims.

The purpose and the effect of the combination product is to enhance and to improve the treatment of the patients, achieving improved clinical effect, safety and quality of life to the patients in clinical practice, compared to using just the particular pharmaceutical products themselves. The purpose and the effect of the invention are fulfilled by several different aspects.

According to the invention, several pharmaceutical products are integrated, in the combination product, through a QAFM, where each included pharmaceutical product in turn is integrated with an adapted question-feedback model (QFM). The specific QFM is developed and adapted based on the clinical characteristics of one single specific pharmaceutical product. The QAFM is adapted to each and multiple included QFM, and hence, each included pharmaceutical product. The QAFM is related and adapted to the combination of the included QFM:s.

One feature of the invention is that the QAFM, and the QFM:s, are developed to improve the clinical effect, the safety concerns, and the quality of life of patients, based on the clinical characteristics of the included pharmaceutical products and the circumstances and conditions of every specific patient.

According to the invention, the QAFM will enable an optimization and individualization of the different included components, such as the QFM:s, the included pharmaceutical products, the adherence and the actual dosage, based upon each specific patient's circumstances, capability and behaviour, in order to achieve an improved clinical effect, safety and quality of life. The optimization and individualization will be performed based upon the answers from each specific patient in relation to existing relevant information regarding clinical use of the actual pharmaceutical products and will be done by the QAFM and the computer program product. For example, a conclusion on such an evaluation can be that a particular patient shall increase the dosage of one pharmaceutical product and remove another. The objective is to achieve concrete increased health for each individual based upon their specific circumstances.

One aspect of the invention concerning the optimization and individualization is to continuously evaluate the health situation of each specific patient based on the input from the patient, concerning his/her behaviour and specific circumstances, in relation to the existing relevant clinical information in clinical studies or clinical practice regarding the used pharmaceutical products, the actual adherence to the pharmaceutical products, the interaction between the included pharmaceutical products, the selected dosing regimens and possible other aspects of the QAFM. Based upon this evaluation the QAFM will respond to the defined users, such as the patients themselves and the healthcare personnel, about the status of the health of the patient and recommended actions, in order to improve the clinical effect, to improve the safety or to improve the quality of life. In this way, the QAFM could, for example, respond with feedback to the relevant users that either a problem has occurred, such as an interaction between two drugs, or a positive change has happened. If a change in the used pharmaceutical products is recommended, it would most probably need to be handled by a physician.

One aspect of the invention is that the QAFM will be able to evaluate the best QFM for each specific patient based upon the specific patient's behaviour and clinical needs in relation to substance combination specific data in clinical studies and clinical practice. The type of feedback will be evaluated, as well, in order to identify and improve the feedback, given to the specific patient. The objective is to use the type of feedback achieving improved clinical effect, safety and quality of life.

One aspect of the invention is that the development of the QAFM should be dependent on each included QFM. It will be central that the QAFM will be related to the content and the characteristics of the included QFM:s and pharmaceutical products.

Another aspect and central component of the invention is that the social behaviour and psychological well-being could be central aspects within the QAFM and the QFM: s. The possibility to interact with both healthcare personnel, as well as other patients, will be an aspect of the invention.

One aspect of the invention is that the computer program product and the QAFM should be able to individualize the treatment to a patient's specific circumstances and personal objectives.

Another central aspect of the invention is to enable and to improve patient safety. The invention will enable early warnings for each user of the invention of possible security alerts concerning the included pharmaceutical products and possible interactions between them, and propose recommended actions to take. This will enable an improved patient safety concerning prescriptions of pharmaceuticals.

One aspect of the invention is that the existing, available knowledge concerning pharmaceutical products forms a fundamental knowledge-base for the development of adapted QFM:s, and QAFM.

One aspect of the invention is that it will be possible for a physician to prescribe a computer program product with different pharmaceutical products included components within the QAFM, instead of just separated, stand-alone pharmaceutical products. The physician will be able to prescribe a product more fully addressing the problems of the patient's total health situation.

Another aspect of the invention is that a product based on the invention will be able to develop and adjust in order to match the guidelines which healthcare is using within a specific therapeutic area. For example, within several cardiovascular diseases guidelines for patients include both multiple identified drugs and recommendations regarding certain life-style changes. A product based on the invention can include variants of these components, making it easier and more efficient for both patients as well as healthcare personnel.

The invention is primarily intended for therapeutic areas in which patients with multiple diagnoses have been prescribed several pharmaceuticals and consequently patient safety is a concern.

Large amounts of data on a pharmaceutical product are collected during clinical trials performed by the manufacturers of the pharmaceutical product. The amount of data is generally too large to be kept in mind of a single person and is summarised by various methods into guidelines for use, such as dosage regimens, counter-indications and risks for side effects and adverse events.

A medical physician prescribing a product based on the invention, as well as a pharmacist selling a prescription or non-prescription of the invention-based product, will have certain knowledge of the product and the included pharmaceutical products. In some countries lacking adequate regulations, pharmaceuticals may even be provided to patients by persons without proper pharmaceutical or medical training. The providing person's knowledge of pharmaceutical products is based mainly on the manufacturer's information, which in turn is based on the summaries of the amount of data collected during clinical trials. The providing person may further be highly specialised in the use of a product, such as a researcher with a special interest in the product and the disease it is aimed to treat, but is more likely to be a practitioner who on a daily basis treats patients with very disparate conditions and diseases. Such a physician needs to be well informed about hundreds of different pharmaceutical products. This entails that certain information, such as recently discovered information or possible interactions, on the product, may be overlooked or unknown to the providing person.

The present invention is based on the realization fact that the integral combination of the pharmaceutical products used, and a specifically adapted system for receiving information from a user of the pharmaceutical products and providing feedback to said user can be used to achieve a number of benefits in clinical practice. In this way, a patient using the integrated package of the pharmaceutical products, and the developed QAFM, can directly benefit from the entire body of knowledge, such as clinical data, related to the pharmaceutical products in the possession of the manufacturer or supplier of the invention-based product, in addition to the information provided by the medical practitioner and/or pharmacist providing the product package. In this sense, the present invention aims to provide a technological support to the patients in order that they benefit from the most recent information about their medication, adapted to their specific situation.

One aspect of the invention is a combination product, or a kit-of-parts, comprising the drug(s) in question and a computer program product comprising instructions causing a computer to provide the patient with the questions, receiving answers to the questions, analysing and processing the answers and providing feedback to the patient.

One aspect of the invention is a method of treatment of a medical condition with the substances having pharmaceutical activities against said medical condition(s) in combination with a computer program product comprising instructions causing a computer to provide the patient with the questions, receiving answers to the questions, analysing and processing the answers and providing feedback to the patient.

One aspect of the invention is to improve the treatment of the patient, based on the invention, where the usage, including dosage and administration, of the included pharmaceutical products are related to the usage.

The above three aspects of the invention shall be considered as equivalent unless specifically indicated otherwise. In particular, the characteristics of the pharmaceutical products and computer program products are the same in all three aspects.

Another aspect of the invention is to make clinically relevant information obtained during clinical use, i.e. clinical trials or clinical practice, of the pharmaceutical products come to the benefit of individual patients in a more efficient way. This is realized by continuously updating the question-analysis-feedback model, the QAFM, implemented in the Computer Program Product by including therein instructions causing the computer to perform a method comprising the steps a) providing a patient and optionally a further respondent with sets of questions according to a question schedule, wherein said sets of questions are adapted to the combination of substances and/or to at least one of the substances in said combination;

b) collecting answers to said questions from said patient and optionally said further respondent;

c) subjecting said answers to a set of functions specific for the sets of questions and the pharmaceutical product thereby generating patient-specific feedback information;

d) providing said feedback information to the patient and optionally to the further respondent;

e) extracting information from said answers and providing said information to a database adapted for storing information collected during clinical use of said combination of substances;

f) providing information stored in said database to a reviser subjecting the sets of questions and/or the sets of functions to a revision based on said information stored in said database;

g) obtaining a revised set of questions and/or a revised set of functions from said reviser; and h) repeating steps a)-g).

i)

The information on which the revision is based can be collected from the individual patient or from more than one patient, preferably at least 50%, such as at least 75% or substantially 100% of patients, clinically using said substance(s) in combination with said computer program product. Revision of the set of functions may include a revision of the feedback information and type of feedback given to the patient.

The reviser performing the revision may be one or more persons skilled in analysis of clinical data and drafting clinical guidelines, such as a team of medical doctors, clinical statisticians and/or pharmacists. It may also be a suitable computer-implemented expert system or set of revision functions. Such a set of revision functions may include comparison of patient parameters and/or patient trend lines with reference parameters and reference trend lines calculated from the information collected from more than one patient, preferably at least 50%, such as at least 75% or substantially 100% of patients, clinically using said substance(s) in combination with said computer program product. Alternatively, the reference parameters and reference trend lines are calculated from information collected only from comparable patients, e.g. patients having the same or similar age, life-style, clinical status, clinical history, sex, ethnicity etc.

The specific information which the database is adapted to store provides the provider of the invention the possibility to collect relevant data from a significant number of patients using the invention in clinical practice and iteratively improve and further adapt the sets of questions and sets of functions to real-life conditions.

One aspect of the invention is to enhance the relation between the specific conditions for each particular patient, both concerning behavioural and physiological aspects, with the clinical conditions for the specific pharmaceutical products concerning used dosage, identified side effects and adverse events, and clinical effect in order to improve individualization. This may be done by including existing clinical research data for the pharmaceutical product(s) in the QAFM, and separate QFM:s, and integrated data of the invention. The individualization may be done in several different ways, including for example an updated QAFM concerning any recommendations of changed dosage or administration or recommendations of changed pharmaceutical products.

One aspect of the invention is to enhance patient adherence to the prescribed dosages or administration regimens and to enhance the clinical efficacy of the included pharmaceutical products. This may be done by including questions on the actual administration; actual dosage; perceived and/or measured therapeutic effects; the relevant life-style factors of the patient; test results and/or perceived quality of life and providing the patient with feedback correlating the positive effects of the pharmaceutical products, and/or the absence or low prevalence of negative effects, with adherence to the prescribed dosage or administration regimen and life-style factors.

One aspect of the invention is to give the user early indications of the occurrence or development of a possible adverse event and/or side effect, by including questions relating to the occurrence or development of a possible adverse event and/or side effect of any of the included pharmaceutical products. This increased awareness of adverse events and side effects results in enhanced protection of patients from adverse events and side effects. This may enable an increased patient safety, which is demanded from authorities like EMA and FDA on pharmaceutical products. This may enable early introduction of pharmaceutical products with an incomplete safety profile on the market, since it allows for making each user of the pharmaceutical product aware of the occurrence or development of a possible adverse event and/or side effect and also facilitates that this may be reported directly to medical staff. It may also enable re-introduction of products withdrawn from the market due to an unacceptably high frequency of adverse events or side effects by making each user of the pharmaceutical product aware of the occurrence or development of a possible adverse event and/or side effect at an early stage.

One aspect of the invention is that the healthcare personnel easily will be able to get an overview report about the health situation of a specific patient, including the aspects of the QAFM, the QFM:s and the included pharmaceutical product(s), and analyzed recommendations of how to improve the clinical effect, safety or quality of life.

One aspect of the invention is that the question-feedback models, QFM:s, are central and necessary parts of the question-analysis-feedback model (QAFM).

One aspect of the invention is to enhance the patient's quality of life.

The computer program product is preferably adapted to be installed on a handheld device, such as a mobile telephone, a smart phone, a Personal Digital Assistant (PDA), tablet computer or similar devices. The computer program product may also be installed on a remote computer, e.g. a. server, web or cloud-based service, and accessible to the user through a computer such as a handheld device, a stationary computer, a laptop or the like. In such a case the feedback is also preferably provided through the same device.

Other aspects of the invention are the computer program product itself and the method performed by the computer program product.

Other aspects of the invention are as provided in the appended claims.

BRIEF DESCRIPTION OF THE DRAWINGS

FIG. 3 illustrates when the further respondent is answering the questions on a separate computer platform 112'.

DEFINITIONS

Figure 1:
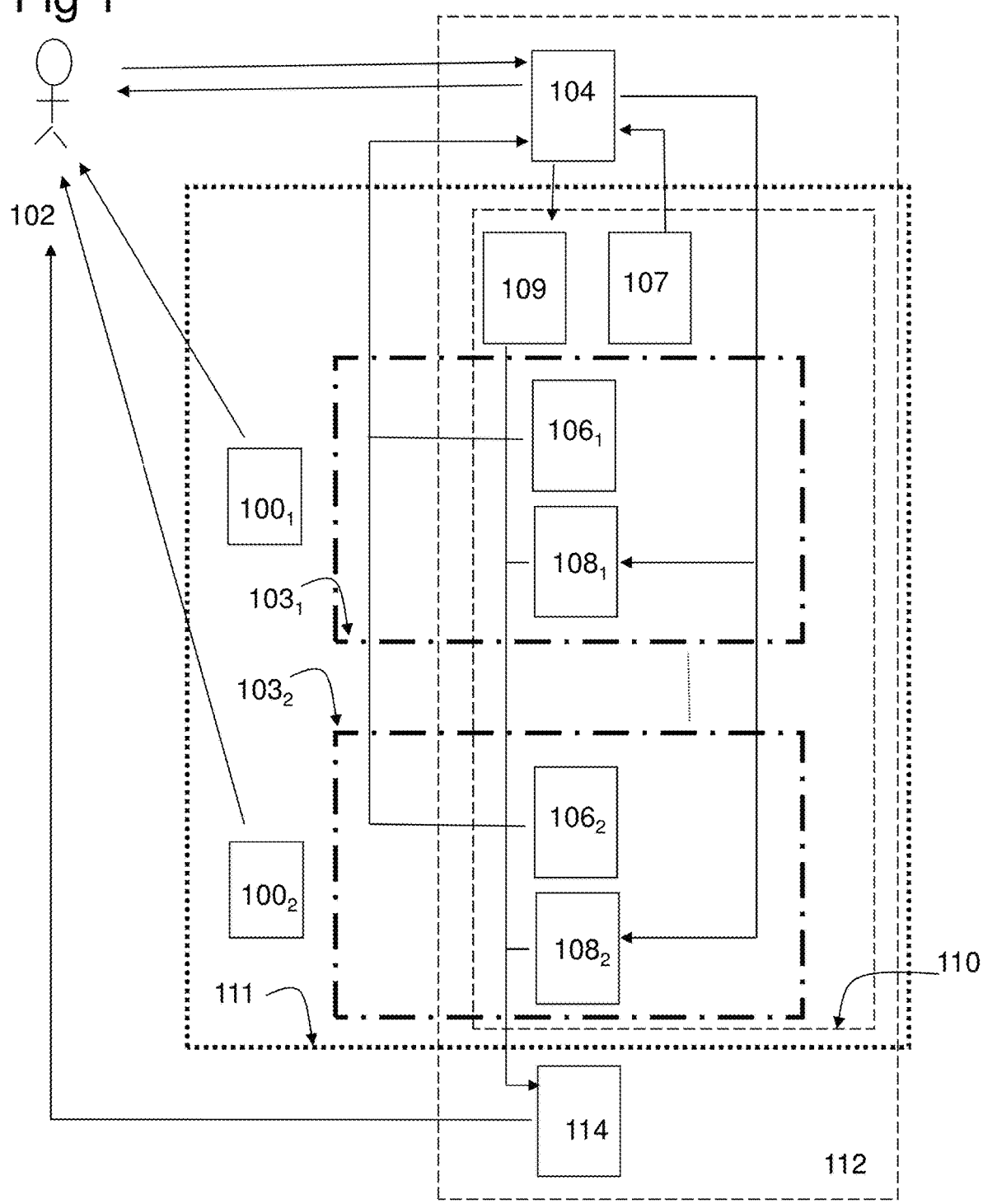
FIG. 1 illustrates the combination product and the structure and usage of two QFM:s ($103_1$, $103_2$) adapted to specific pharmaceutical products ($100_1$, $100_2$), in relation to one QAFM (110) and the patient (102). 107 denotes the set of questions of QAFM and 109 the set of functions (analysis part) of QAFM. 112 denotes the computer platform used for interaction with the respondent.

All words and terms used in the present specification are intended to have the meaning usually given to them in the relevant art. However, for the sake of clarity, a few terms are specifically defined below.

The term "set of questions" is a questionnaire with predetermined questions or items shown to a respondent to get answers for feedback purposes. The questions within the set preferably have a limited number of possible answers, such as yes/no; scale 1-10; multiple choice; etc. The questions may however also have an undefined number of answers, such as a value of a test parameter (e.g. blood pressure, blood glucose level).

The questions in the set of question are posed to the respondent according to a certain regimen or schedule. This is denoted a "question schedule" or "question regimen" in the present application. These terms are intended to be equivalent if not otherwise indicated.

The term "set of functions" means a set of functions that can be applied to the answers to a set of questions to extract specified information and generate feedback based on the answers.

The combination of a set of questions and a set of functions is referred to as a "question-feedback model", sometimes abbreviated "QFM".

The combination of several included QFM:s, as well as the combination of another set of questions, another set of functions and the type of feedback, is referred to as a "question-analysis-feedback model", sometimes abbreviated "QAFM".

The QAFM and the QFM:s could together, as a group, be denoted as the "model".

That a set of questions is "specific" to a certain pharmaceutical product shall be construed to mean that it comprises questions that are applicable and clinically relevant to the pharmaceutical product. The individual questions, and the set of questions in total, are preferably more applicable and clinically relevant to the pharmaceutical product in question than to any other pharmaceutical product.

The term "respondent" is used to denote the individual responding to a question.

The term "patient" is used to denote the individual using the pharmaceutical product.

The terms "computer application" and "computer program product" shall be considered equivalent unless specifically indicated otherwise.

The terms "pharmaceutical product" and "medical product" shall be considered equivalent unless specifically indicated otherwise. These terms refer to pharmaceutically acceptable compositions of pharmaceutically active substances (drugs) intended for administration to a patient.

The term "side effect" means a secondary and potentially adverse effect of a drug or treatment.

The term "adverse event" means an adverse outcome that occurs during or after the use of a drug or other intervention but is not necessarily caused by it.

"Clinical use" shall be construed as the use of the pharmaceutical product and/or the life style factor by individual subjects. It includes the use of the pharmaceutical product in Phase II, III and IV clinical trials and the use of the product in patients in clinical practice (sometimes referred to as real life).

"Clinically relevant information" shall be construed as information relevant to the clinical characteristics of a pharmaceutical product, e.g. on effect, side effects, counter-indications, metabolism etc. Such information is extensively collected during clinical trials.

DETAILED DESCRIPTION OF THE INVENTION

The main aspect of the present invention is a combination product comprising two or more pharmaceutical products and a computer program product comprising instructions to perform a method comprising the steps of providing a defined set of specific questions to the user, collecting answers to the questions and analysing, transforming and processing the answers by way of a defined set of specific functions to generate feedback to the patient.

By adapting the combination of the set of questions and the set of functions, which combination is hereinafter called the "question-feedback model", to be adapted to one pharmaceutical product, and optionally the therapeutic indication and/or prescribed dosage/administration regimen, it is possible to achieve clinical improvements in the therapeutic effect of the pharmaceutical product and quality of life for patients. By adapting the combination of two, or more pharmaceutical products, and the corresponding adapted QFM:s, into a model called the "question-analysis-feedback-model" (QAFM), it is possible to achieve an even higher, unexpected and significant improvement in the therapeutic effect of the pharmaceutical products and quality of life for patients. Without being bound by theory, the improved therapeutic effect within the area of the included pharmaceutical products and quality of life, may be due to improved individualization concerning patient specific conditions and clinical aspects of the pharmaceutical products, due to improved adherence by the patient to the prescribed administration and/or dosage regimen, due to improved awareness of other factors influencing the relevant condition being treated with the pharmaceutical products, or due to a placebo-like effect.

For each combination of the computer program product and one pharmaceutical product a question-feedback model is developed and adapted to the specific characteristics of the pharmaceutical product and the behavior of the patients within the actual therapeutic area(s). The development of the question-feedback model follows the same general rules for different types of pharmaceutical products, but the specific question-feedback models will be different due to the characteristics of the pharmaceutical product and its clinically relevant information.

For each combination of several pharmaceutical products and the adapted QFM(s), a QAFM is developed and adapted to the specific characteristics of the included pharmaceutical products and the behavior of the patients within the actual therapeutic areas(s). The development of the QAFM follows the same general rules for different types of pharmaceutical products and therapeutic areas, but the specific QAFM will be different due to the characteristics of the pharmaceutical products, its clinically relevant information and the patient behavior.

The question-feedback model, QFM, comprises the following parts, of which all are adapted for the clinical effect of the pharmaceutical product:

A set of questions
A set of functions
The type of feedback

The set of questions is implemented in a questionnaire giving the respondent the ability to choose any of a number of possible answers to each question or enter a number representing a test value.

The questions may relate to the following, the list being illustrative and non-exhaustive:

Side effects and adverse events, such as adverse drug effects
Adherence to dosage and/or administration regimen, such as if or when the pharmaceutical product has been administered; or which dose was administered.
Symptoms, such as stiffness; swelling of limbs or joints; headache; pain; blood in excrement; incontinence; fever; urticaria; rashes; skin irritation; itching; dryness of mouth; shortness of breath; coughing; sneezing; rhinitis; anxiety; irritation; restlessness; dizziness; fatigue symptom
Dietary intake, such as meal size; meal frequency; type of diet; satisfaction with diet
Exercise, such as type, duration, frequency or avoidance of physical exercise Mood, such as if the respondent feels happy, sad, depressed, anxious, restless, etc.

Sleep, such as if the patient has slept well; duration or quality of sleep [Ref: Torbjörn Åkerstedt; The importance of sleep for health and work]

Use of tobacco, alcohol and other drugs, such as type and amount of use; addiction; intention or inclination to quit use; progress or lack of progress in cessation Stress, such as perceived stress level; amount of personal quality time or spare time; amount of family quality time; stress at work Body functions, such as the function of the gastrointestinal system; mental capacity, muscle strength/weakness; cardiovascular capacity; physical capacity Treatment, such as if the treatment perceived is working well; motivation to start or continue treatment Quantitative test results, such as blood pressure; body fluid; blood tests or excrement analysis results; body weight; Body Mass Index; pulse etc General, such as quality of life; feeling of support from family, friends, caregiver The questions within the set preferably have a limited number of possible answers, such as yes/no; Visual Analogue Scale (VAS); Likert scale; multiple choice, including symbols (such as "happy face" and "sad face" to capture mood); etc. However, the questions may also have an undefined number of answers, such as a value of a test parameter (e.g. blood pressure, blood glucose level, body temperature, weight) or free text.

Generally, the questions are posed to the patient using the invention based product because only the patient has the true first-hand knowledge of his/her situation. However, in addition to questions posed to the patient, further questions may be posed to other respondents. These may include family members, relatives or other persons close to the patient. This may be particularly useful for pharmaceutical products used in treatment of psychiatric disorders where the patient's assessment of his/her situation may be incomplete and observations made by another person may be valuable. Questions to be answered by other respondents may belong to the same set of questions as those answered by the patient, but may be implemented in a separate questionnaire.

The specific questions and invitations given to the respondents and the type of questions are adapted to the specific characteristics of the pharmaceutical product and the behavior of the patients within the therapeutic area in order to optimize the clinical effects.

When defining the actual questionnaire it is preferable to develop questions to the respondent in order to identify possible upcoming adverse events, or indications of adverse events, as well as possible upcoming side effects with the purpose of increasing patient safety of the included pharmaceutical product.

In addition to the set of questions, also a regimen for asking the respondent questions should be developed, including which questions are compulsory to answer, optionally before or after a certain time or within a certain time interval; the questions which may be left unanswered; at what time of the day the questions will show up for the respondents to answer; with what frequency the questions shall show up etc. The regimen can be static over time but also change, e.g. the frequency of questions can decrease with time or change depending on the respondent's answers.

In addition to the above described questions it may be advantageous to include messages, which cannot be answered, to the respondent. Such messages may include recommendations, suggestions or information intended to motivate the respondent, e.g. to continue the prescribed dosage regimen although symptoms have disappeared or are less pronounced.

It may furthermore be advantageous to adapt the set of questions and messages and the regimen for asking the questions and providing the messages with regard to cultural differences and the language of the user. Principles for the translation and cultural adaptation process for PRO measures have been described (Wild D, et al., Value Health 2005; 294-104) and may be adapted to the present invention by the skilled person.

The question-feedback model, QFM, further comprises retrieving answers from the respondents in a predefined format suitable for input into the set of functions for generating feedback.

The question-feedback model, QFM, further comprises a set of functions to generate patient-specific feedback based on the answers of the respondent or respondents. These functions may comprise:

Calculations resulting in a realistic target for a specific patient to achieve. The target could be based on information given from the results from earlier clinical trials concerning the pharmaceutical product or other existing relevant information from clinical practice. Then the target can, for example, be illustrated as a continuous graph of the predicted development for the patient, given that the prescribed administration or dosage regimen is followed. The illustration of this continuous graph would vary between different pharmaceutical products and therapeutic areas. In some areas it will illustrate the improvement of the condition whereas in other areas, for example, COPD (Chronic Obstructive Pulmonary Disease) where patients slowly feel worse, it will illustrate the lack or relative slowness of feeling worse.

Calculations of future predictions for a specific pharmaceutical product and patient, based upon earlier answers from the patient and results from clinical trials and answers from other patients in clinical practice using the actual pharmaceutical product, for example external web and data sources. These future predictions can, for example, be several predictions for each patient, based upon different circumstances in the shape of how the patient changes his/her behavior. An example of this will be if the patient increases the adherence to the specific pharmaceutical product the patient and thereby will develop in a more positive way concerning specific symptoms of the disease.

Knowledge and rules using, for example, methods for Computer Adaptive Testing and Item Response Theory including the adapted databank with the purpose of optimal individualized and personalized medicine. This can, for example, result in an individualized questionnaire for each patient based upon their own characteristics and behavior.

Calculation of trend lines based upon the specific pharmaceutical product and the answers given by the patient.

Rules and thresholds for defining when to give notifications concerning the pharmaceutical product and different kind of issues, e.g. possible adverse events, possible side effects, change dosage regimen, possible interaction of other prescribed drugs etc. These have to be carefully developed and have to take notice of possible combination between different questions, the evolvement of the answers from patients over time, other possibly used medication, etc.

Patient-specific feed-back is generated by the above described set of functions based on answers supplied by the patient. The feedback may be provided through any medium favorable to the patient, e.g. through a website, a handheld device (mobile phone, smart phone, tablet computer, PDA, etc), paper, voice, e-mail, fax, SMS, or corresponding type of message etc.

Examples of feedback are:

Graphs illustrating the answers given by the patient on different selected questions. The graphs may, among other things, illustrate how the patient has evolved over time.

Illustrating the answers from the patient in combination with calculated values such as the targets for the patient. The purpose of this type of feedback is, for instance, to motivate the patient to continuous improvements.

Illustrations of how the patient's health status is evolving in comparison to the evolvement of earlier patients using the same pharmaceutical product, for example patients in clinical trials other existing relevant clinical information from clinical practice.

Illustrations of how the patient's health status can evolve and the result of it as a future prediction, based upon how the patient continues to handle his/her health situation and data from clinical use of the pharmaceutical product. For example, graphs can be used to show how the patient may evolve if the patient increases the adherence to the medication of the pharmaceutical product.

The, preferably de-identified, answers from the patient in relation to calculations based upon information given from other patients in clinical practice using the pharmaceutical product, specifically selected for the actual circumstance. The purpose of this is, among other things, to encourage the patient to increase his/her personal health status.

Message sent based upon notifications from the algorithms. This can, for example, be messages concerning possible adverse events, or indications of possible side effects, or possible conclusions that a new dosage for the actual pharmaceutical product may be needed, or positive feedback to the patient to encourage a behavior leading to e.g. better adherence or increased quality of life. Exemplary messages can include messages that the used dosage of the pharmaceutical product ought to be changed, or that the first signs of a side effect appear to be showing and that the patient should be aware of these signs. The invention will hence enable a faster change of used medicines by patients experiencing an adverse event. The patient can receive messages from the healthcare personnel as well as through the computer program product, as a result of the feedback.

The questionnaire given to the patient can change based upon the algorithms for CAT and IRT (see above), or other appropriate algorithms or computer implemented methods, in order to individualize the questions for the characteristics of each patient and the pharmaceutical product.

Optionally, feedback may also be provided to other than the patient, such as the health care staff (e.g. treating medical practitioner or nurse, pharmacist etc.). Such feedback may include:

Results from notifications from the algorithms, e. g. when an adverse event or a side effect has occurred. This information can, for example, be sent to the responsible healthcare provider and/or authorities such as the Medical Products Agency. The healthcare personnel will then be able to take appropriate adjustments. The graphs and illustrations presented above can be given to the responsible healthcare personnel as well.

Results from continuous results in clinical practice based upon the answers given by the patients. The invention could hence improve clinical research through continuous follow up of a huge amount of patients for the specific selected pharmaceutical products. The information/answers from the patients will be de-identified and returned to the researching organization. The purpose is to utilize the enormous information in real clinical practice in order to develop improved pharmaceutical products and treatments for patients.

The continuous follow-up of the results from patients will also result in possibilities for an easy evaluation between different kind of treatments, both from a medical and an economic perspective.

The question-feedback model, QFM, may be adapted to the specific pharmaceutical product by using the information on the pharmaceutical product available from clinical trials carried out in preparation for an application for marketing approval for the pharmaceutical product. Such trials are designed to find all relevant information about the pharmaceutical product and that information can be used to design the set of questions with applicable answers, the set of functions for generating the feedback from the answers, and the form of feedback provided to the patient. The continuous development of the QFM, for a specific pharmaceutical product, will also take into consideration relevant knowledge from clinical practice concerning the specific pharmaceutical product, other studies, patient behavior concerning the specific pharmaceutical product, etc.

Information on the normal effect of the pharmaceutical product can be used to provide the patient with feedback on how he/she achieves a better or worse effect than normal when using the pharmaceutical product. It may also be used to give the patient feedback on how the treated condition will have developed if the pharmaceutical product had not been used, or used to a different extent than the patient actually is using it.

Information on known possible side effects may be used to include questions giving early feedback on occurrence of side effects, which may guide the user to change or cease the administration or dosage regimen according to guidelines based on the information about the side effects, or to contact the treating physician if advised.

Information on known counter-indications for using the pharmaceutical product may be used to include questions giving early feedback warning for possible side effects or adverse events. It may be that during treatment with the pharmaceutical product the patient contracts a condition which may lead to an adverse event or side effect in combination with the pharmaceutical product. If such risks are known, it is possible to include questions resulting in feedback making the patient and optionally the treating physician aware of this complication, which may lead to an adjustment or change in treatment implying an improved patient safety of the pharmaceutical product.

For example, an earlier registered pharmaceutical product indicated for treatment of obesity was known to worsen depressions. The majority of questions and feedback in a question-feedback model for an obesity drug would probably focus on diet, physical activity, weight loss and the like. The inclusion of one or more mood-related questions would however been able to indicate early if the patient was at a risk of developing a depression which would have been a strong indication to the patient to cease the administration of the actual pharmaceutical product. These questions should have been specifically designed to retrieve relevant information on the types of mood-related adverse events or side effects associated with the specific pharmaceutical product.

Optionally, additional information not supplied directly by the patient can be used. This may include:

Information from performed clinical trials. This can, for example, be the result of how the included patients in the clinical trials using the actual pharmaceutical product responded to the pharmaceutical.

Information from other patients in clinical practice. This can, for example, be the result and answers given by other patients in clinical practice? using the same pharmaceutical product and how they respond to the pharmaceutical. Using this information, a common index of how a huge amount of patients react upon the actual pharmaceutical product in clinical practice can be evaluated, for instance.

Information from other products and systems, such as administration systems, laboratory data, personal patient devices such as watches, heart rate monitors, scales, mobile phone applications, pedometers, glucose meters, thermometers, audiometers, inhalers, ultrasound devices, electrocardiography devices, etc. Such information can automatically be collected by or transferred to the computer program product by different means.

For each combination of a specific pharmaceutical product and the computer program product a candidate specific question-feedback model, QFM, has to be developed. This candidate model has to be developed based on all considerations mentioned above.

The development of the candidate question-feedback model, QFM, includes the following steps:

A suitable set of questions is identified and developed. The intention is to develop an optimal set of questions and normally this is an iterative process. In this, the following aspects should be considered, as well as the concerns mentioned above describing what is included in the set of questions.

The set of questions should be designed based upon the specific clinical circumstances of the pharmaceutical product concerning the existence of possible adverse events, possible side effects and the therapeutic effect.

The set of questions should be designed based upon the special circumstances of the patient category of the actual therapeutic area.

The set of questions should be designed in order to improve the behavioral aspects of the patients. They should increase the possibilities for enhanced clinical effect and patient safety of the specific pharmaceutical product, and the quality of life for the patients.

The questions should be easy to understand and encourage the patient to answer them. The suitable and optimal structure type of questions should be used, i.e. VAS, Likert scale, free text, multiple choice, etc.

The amount of questions should be minimized in order to simplify for the patients.

The proper regimen for asking the respondent questions should be developed. The following should, for example, be defined:

When the questions should appear in the patient's device, for instance which specific day and what time during the day Which questions that should be compulsory to answer The frequency of how often the questions should appear in the patient's device Which questions that should be able to individualize, i.e. to add or remove, and to which extent. For example, some questions could be able to appear more or less seldom, i.e. changing the frequency of the question.

Whether, and in which way, the set of questions should be individualized and adopted based upon the patient and the pharmaceutical product specific clinical conditions. This could involve how the questions should be answered, selection of media, etc, with the purpose of improving the clinical effect and patient safety of the specific pharmaceutical product.

A suitable set of functions is identified and developed. The intention should be to develop an optimal set of functions and normally this is an iterative process. In this, the following aspects should be considered, as well as the concerns mentioned above describing what is included in the set of functions.

The set of functions should be designed based upon the specific circumstances of the pharmaceutical product concerning the existence of possible adverse events, possible side effects and the therapeutic effect.

The set of functions should be designed based upon the special circumstances of the patient category of the actual therapeutic area.

The set of functions should be designed in order to improve the behavioral aspects of the patients. They should increase the possibilities for enhanced clinical effect and patient safety of the specific pharmaceutical product, and the quality of life for the patients.

The set of functions should be developed based upon which type of information that is possible to use considering the specific pharmaceutical product, e.g. if there are information from earlier clinical trials and/or if information from other patients in clinical practice, that can be utilized.

The set of functions should be developed based upon whether knowledge and rules from methods using Item Response Theory and Computer Adaptive Testing, or other appropriate algorithms or computer implemented methods, are available.

The set of functions concerning rules and thresholds, for example with the purpose of avoiding possible adverse events and/or side effects, giving positive feedback and optimizing the dosage regimen, should be developed concerning the circumstances of the pharmaceutical product, performed clinical trials and the specific patient population.

The set of functions could contain rules of which questions should be related to specific thresholds, for example if a threshold is reached by a patient, which questions should then appear or which type of feedback should be given.

The set of functions could contain dependencies between certain questions and the functionality and rules of the dependencies, e.g. if a patient answers a specific alternative on one question another specific question appear, otherwise another question will appear instead.

The set of functions could contain the administration rules concerning different intervals when specific questions will appear based on a certain threshold, which could be time or that a criterion has been fulfilled. An example of this is that during a first period of time the patient could have a certain set of questions, and after a certain period of time, which could be a couple of weeks or months, the set of questions changes into another version. The set of questions could also be changed due to a certain threshold has been fulfilled, for example a certain level of blood pressure or the level of HbA1c is reached.

A suitable type of feedback should be identified and developed. The intention should be to develop an optimal type of feedback and normally this is an iterative process. In this, the following aspects should be considered, as well as the concerns mentioned above describing what is included in the type of feedback:

- The type of feedback should be designed based upon the specific clinical circumstances of the pharmaceutical product concerning the existence of possible adverse events, possible side effects, and the therapeutic effect.
- The type of feedback should be designed based upon the special circumstances of the patient category of the actual therapeutic area.
- The type of feedback should be designed in order to improve the behavioral aspects of the patients. They should increase the possibilities for enhanced clinical effect and patient safety of the specific pharmaceutical product, and the quality of life for the patients.
- It should be defined which type of feedback that should be given and to whom.
- The type of feedback should be designed and developed based upon to whom and which type of feedback that should be given.
- The type of feedback should be designed and developed based upon the developed set of questions and set of functions for the specific question-feedback model, QFM.
- The type of feedback could be designed in order to improve the clinical effect and patient safety of the specific pharmaceutical product in using the given thresholds
- The type of feedback could be designed in order to improve the clinical effect and patient safety of the specific pharmaceutical product by individualizing the dosage administration of the specific pharmaceutical product to the conditions of the patient The question-analysis-feedback model, QAFM, comprises the following parts:

- A set of questions, which contains identical logical parts, structure and aspects, as well as an identical development process, as the one described above for the QFM
- A set of functions, which contains identical logical parts, structure and aspects, as well as an identical development process, as the one described above for the QFM
- The type of feedback, which contains identical logical parts, structure and aspects, as well as an identical development process, as the one described above for the QFM
- The included QFM:s Examples on differences between the QAFM and the QFM are, the list being illustrative and non-exhaustive:

- The set of questions within the QAFM should be adapted for all included pharmaceutical products and their adapted QFM:s.
- The type of questions given to the respondents, as well as the performed analysis, the set of functions and the type of feedback, are adapted to the specific characteristics of all the included pharmaceutical products, the therapeutic area(s) and the behavior of the patients in order to improve the clinical effect, patient safety and quality of life of the patients. The set of functions could be used as an analysis component evaluating all the included components within the QAFM in order to improve the clinical effect, the safety and quality of life of the patients. For example, the results of the analysis by the set of functions could result in a recommendation to the users to reduce the use of one component, such as the dosage of an included pharmaceutical product and instead increase the usage of another component, such as increase the dosage of another pharmaceutical product.

The set of functions, as well as the type of feedback, in the QAFM may relate to the following, the list being illustrative and non-exhaustive:

- Evaluation aspects of the included pharmaceutical products and their corresponding QFM:s, based upon perceived clinical effect and side effects/adverse events.
- Evaluation in order to improve the clinical effect, the patient safety and patient quality of life
- Evaluation and feedback to the users in order to optimize the included components for the specific patient based upon his/her behavior and adherence to included components
- Evaluation of patient specific information according to the above, in relation to existing clinical information, i.e. data from earlier performed clinical studies and clinical practice, concerning the included pharmaceutical products When developing the QAFM set of questions, the set of functions and the type of feedback considerations should be done in order to optimize the total questionnaire and the feedback for the simplicity of the patients. The development of the QAFM will be iterative and similar to the development of the QFM, clearly adding the further aspects of the QAFM in relation to the QFM, such as the evaluation of the pharmaceutical products and their adapted QFM:s.

It may be desirable to furthermore optimize the set of questions and the feedback for use on a certain computer platform. For instance, if the respondent will use a simple mobile telephone the questions will be adapted so that they can be answered simply by pressing buttons 0-9 and yes/no/up/down and feedback may be provided in short text messages and simple graphs. If the respondent uses an advanced mobile telephone or tablet computer the questions may be constructed to give more complex answers and still be easy to use, and the feedback may also be made more complex, such as color-coded graphs and longer messages.

The candidate QAFM including the QFM:s is then validated in one or more steps. The validation of the model aims to evaluate and ensure the therapeutic effect of the integrated combination of the computer program product and pharmaceutical products, minimize the amount of adverse events and side effects, and increase the quality of life for the patients. The evaluation of the clinical effect and the value of the candidate QAFM including the QFM:s for specific pharmaceutical products are preferably performed through clinical trials, which is usually referred to as a Phase II clinical trial or a corresponding study. In this the candidate model for the pharmaceutical products is evaluated regarding clinical efficacy such as positive medical effect and increased security level for the combination product.

There are a number of types and designs of clinical studies and a skilled person will be able to choose a type of study and design well suited to achieve the aims as outlined herein. The clinical studies or corresponding study will be designed to focus to prove the following of the model enabling the combination of the computer program product and the pharmaceutical products:

achieve improved clinical effect of the combined product based on the invention achieve improved level of safety for patients increase quality of life for the patient Based on progress and results from clinical studies and clinical practice, the QFM and QAFM may of course be adjusted or revised in order to improve its clinical effect, safety or aspects of quality.

The combination of the models and pharmaceutical products may also be compared to existing approved treatments in Phase III-type clinical trials before being put on the market.

The question-feedback model, and the question-analysis-feedback model are implemented in one or more computer-program products running on one or more computer platforms, wherein the computer program product and the computer platform together have means for providing the set of questions, for receiving the answers, for applying the analysis and the set of functions to generate the patient-specific feedback and preferably also for providing said feedback to the patient.

The computer program product may be supplied on a suitable carrier together with the pharmaceutical product, as a kit-of-parts. Suitable carriers are well-known to the skilled person and depend on the platform on which the computer program product shall run, but includes without limitation, CD-ROM, USB-memory sticks, flash memory cards. The computer program product may also be made available to the end user separately from the physical pharmaceutical product. This can be done e.g. by supplying information on how to access the computer program product on a remote server and install the computer program product on the relevant platform with the pharmaceutical product. The computer program product can also be run on a remote server and be accessed via an internet service using a user interface like a web browser or client application for the relevant platform. Ways of accessing and implementing the computer program product can also include barcode scanning techniques. The computer program product may be included in the kit-of-parts in the form of instructions for accessing and/or installing the computer program product from a remote location, such as a remote server. Information about how to get started with the computer program product and how to use it can be given in the instructions related to the pharmaceutical product or the computer program product.

If the computer program product is made available separately from the pharmaceutical product, a unique identifier may be provided with each individual kit. The identifier may be used to confirm that the respondent has got the correct combination of computer program product and pharmaceutical product and to confirm that the respondent has the right to use the computer program product.

The computer program product is an essential part of the main aspect of the invention and is itself one aspect of the invention, as is the method implemented in the computer program product.

The pharmaceutical product may be any pharmaceutical product for which there exists a preferred or prescribed administration and/or dosage regimen. This includes all pharmaceutical products that have been approved for marketing based on results of clinical trials defining a therapeutically effective dose or dose range and pharmaceutical products for which a medical or other practitioner prescribes an individual administration or dosage regimen to an individual patient based on information supplied by the manufacturer of the pharmaceutical product. It furthermore includes pharmaceutical products for which an application for marketing approval is to be submitted, pending, or has been refused. The pharmaceutical product may or may not be subject to regulation by a Medical Products Agency or other governmental agency, it may be a prescribed medication, an over-the-counter product or any other allegedly therapeutically active product, such as a herbal medicinal product.

Examples of pharmaceutical products that can be used in the present invention are, the list being illustrative and non-exhaustive (trade names within parentheses): Aripiprazol (Abilify), Rimonabant (Acomplia), Pioglitazon (Actos), glucoseamine (Glucosine), Octocog alfa (Advate, Advair), Flutikason in combination with Salmeterol (Seretide), zolpidem (Ambien, Stilnox), Insulin glulisin (Apidra), Donepezil (Aricept), irbesartan (Avapro, Aprovel), rosiglitazone (Avandia), metformin in combination with rosiglitazone (Avandamet), glimepiride in combination with rosiglitazone (Avandaryl), bevacizumab (Avastin), Interferon beta (Avonex), Darbepoetin alfa (Aranesp), anastrozole (Arimidex), Kandesartan (Atacand), olmesartan (Benicar, Olmetec), Interferon beta-1b (Betaseron), Interferon beta (Betaferon), exenatide (Byetta), Bikalutamid (Casodex), Celecoxib (Celebrex, Celebra), Escitalopram (Cipralex/Lexapro), duloxetine (Cymbalta), Vareniklin (Champix), Glatiramer (Copaxone), Carvedilol (Coreg), Losartan (Cozaar), Rosuvastatin (Crestor), Ramipril (Tritace), Valsartan (Diovan), Venlafaxin (Efexor), oxaliplatin (Eloxatin), Etanercept (Enbrel), raloxifene (Evista), ezetimibe (Ezetrol, Zetia), Tamsulosin (Flomax, Flomaxtra, Urimax), fluticasone (Flovent, Flixotide), Alendronic acid (Fosamax), Gemcitabine (Gemzar), imatinib mesylate (Gleevec, Glivec), Trastuzumab (Herceptin), insulin lispro (Humalog), Adalimumab (Humira), Lopinavir/ritonavir (Kaletra), Sumatriptan (Imitrex, Imigran), Sitagliptin (Januvia), insulin glargin (Lantus), Fenofibrate (Lipanthyl, TriCor), atorvastatin (Lipitor), Insulin Detemir (Levemir), amlodipine and benazepril (Lotrel), Leuprorelin, (Lupron, Leuplin), pregabalin (Lyrica), rituximab (Mabthera, Rituxan), Telmisartan (Micardis), Esomeprazole (Nexium), amlodipine (Norvasc), insulin aspart (NovoLog, NovoMix, NovoRapid), repaglinid (NovoNorm), Rabeprazole (Pariet), paroxetine (Paxil, Seroxat), Pantoprazole (Protonix, Pantozol, Pantoloc), Clopidogrel (Plavix), pravastatin (Pravachol), Epoetin Alfa (Procrit, Eprex), takrolimus (Protopic), budesonid (Pulmicort), interferon beta-1a (Rebif), sibutramin (Reductil), Infliximab (Remicade), Risperidon (Risperdal), Metoprolol (Seloken, Toprol), quetiapine (Seroquel), Tiotropium (Spiriva), budesonide and formoterol (Symbicort), Montelukast (Singulair), Docetaxel (Taxotere), Topiramat (Topamax), Emtricitabin and Tenofovirdisoproxil (Truvada), ezetimibe and simvastatin (Vytorin), bupropion (Wellbutrin), Betametason in combination with Kalcipotriol (Xamiol) calcipotriene (Taclonex), simvastatin (Zocor), Sertralin (Zoloft), zoledronic acid (Zometa), Olanzapin (Zyprexa), cetirizine (Zyrtec), ticagrelor (Brilique).

The invention will now be described in relation to the appended drawings.

FIG. 1 shows a combination product (111) according to claim 1 wherein N=2, comprising two pharmaceutical products (100$_1$, 100$_2$) available to a patient/respondent (102), and a computer program product (110). Two sets of questions (106) and two sets of functions (108), one for each QFM (103), together with a set of questions (107) and a set of functions (109) of the QAFM, for converting the answers to the questions into patient feedback are implemented in the computer program product (110) running on a computer platform (112) having means (104) for interacting with patient/respondent 102, i.e. posing questions and receiving answers to said sets of questions (106) and (107), from said patient (102) and send the answer information to the sets of functions of the QAFM (109) and QFMs (108$_1$, 108$_2$). The computer platform further has means (114) for receiving patient feedback from the sets of functions (108) and (109), and communicating said feedback to said patient (102).

Figure 2:
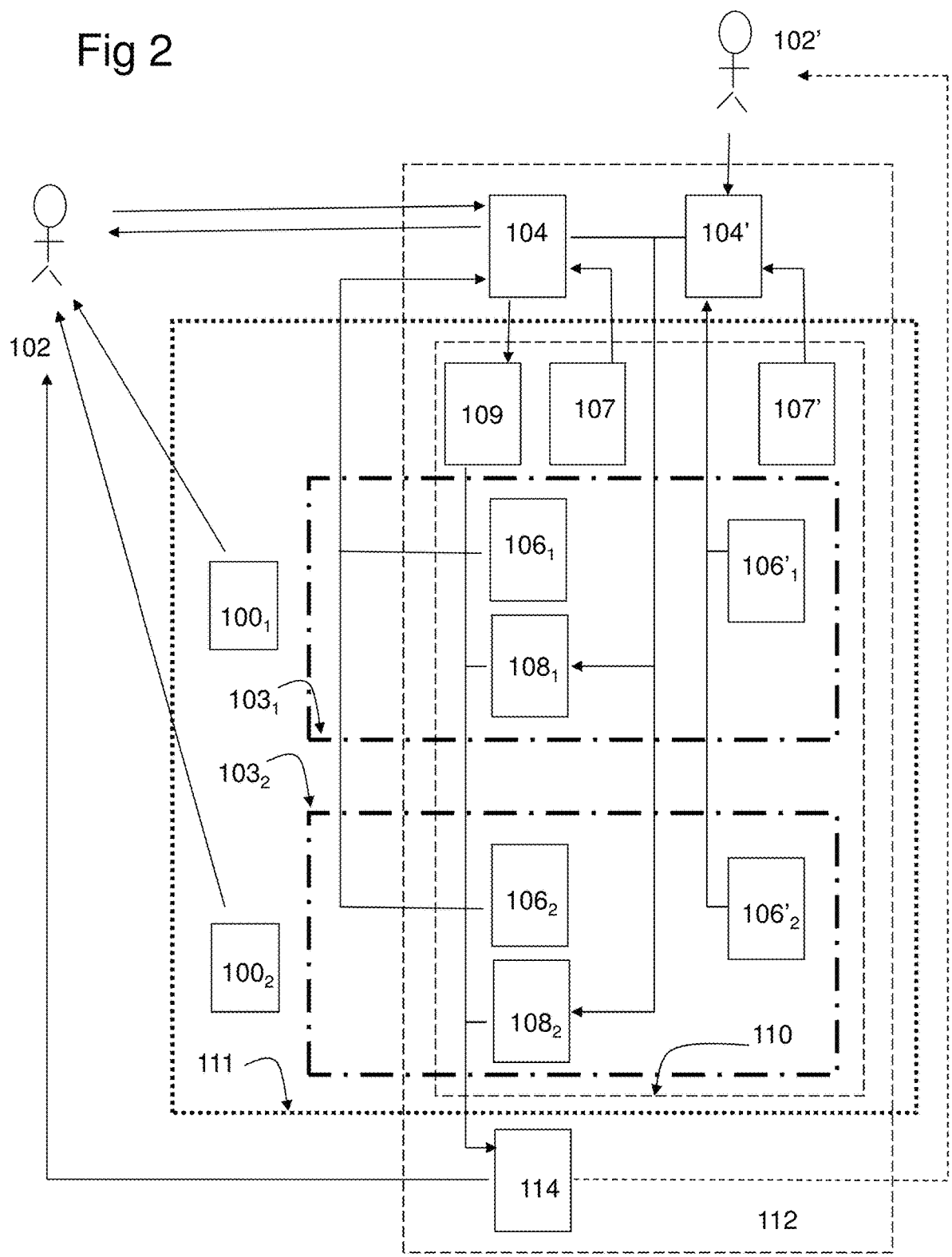
FIG. 2 illustrates the two QFM and the QAFM when adding a further respondent 102'.

FIG. 2 shows an alternative embodiment of the invention, wherein a further respondent (102') answers further sets of questions (106') for the QFM and (107') for the QAFM through means (104') for receiving answers to said sets of questions from said further respondent. The answers to the sets (106') and (107') are then provided together with the answers to the sets (106) and (107) to the sets of functions (108) for the QFM and (109) for the QAFM respectively to generate feedback to patient (102) through computer platform means (114) for receiving patient feedback from the sets of functions (108) and (109) and communicating said feedback to said patient (102). Optionally, feedback is also provided to the further respondent (102'), shown with a dotted line. The further respondent may be a person close to the patient, such as a family member. The means (104') for receiving answers from the further respondent may be implemented on a separate computer platform (112'), cf FIG. 3.

The example below serves to further illustrate the invention, provide experimental support and enable the skilled person to implement the invention. It shall not be construed as limiting the scope of the invention, which is that defined by the appended claims.

Examples

Study 1

A study is to be performed according to the following description in order to exemplify and show the clinical effect of the invention.

In the study the combination product, a computer program product (CPP) integrated with two pharmaceutical products (PP:s), using an adapted question-analysis-feedback model (QAFM) and two question-feedback models (QFM:s), should be evaluated versus only the two separate PP:s. The purpose is to evaluate different aspects in order to show the effect of the invention. The objective of the study should be to evaluate the clinical effect of a combination of two PP:s and a CPP, in relation to only the two PP:s. The integration in the combination product should be done through a QAFM and two QFM:s. The actual therapy area is type 1 diabetes and the effect variable should be the level of HbA1c. The actual PP:s are Apidra and Lantus. In the study the used model should consist of the following parts:

A set of questions for the QAFM and two for the QFM:s. Some of the characteristics:
Developed based on the specific aspects of the PP:s and the patient category.
One compulsory group of questions to be asked, which should be given to all patients, and one optional group of questions to be asked if they were relevant for the individual patient.
The questions should be individualized depending on the patients' specific conditions and situation. For example, specific questions should be added or removed depending on specific patient conditions.
Different type of questions, i.e. multiple choice, VAS, etc.
Both compulsory and optional questions to be answered.
The questions should be integrated with a question schedule with response times. The response times should include automatic reminders (alerts) in the CPP on the mobile phones to remind the patients to answer the questions. The question schedule should be developed so only the questions valid for each response time show up in the CPP and be possible for the patient to answer. This feature should secure that the patients answer the right questions at the right time. The question schedule should be individualized depending on the patient's daily schedule.
The questions should be presented to the patient on the patient's mobile phone. The illustration (see FIG. 1) shows the user interface of the implemented questions and feedback.

The sets of functions in the model. Some of the characteristics:
Calculations on the data, consisted of the answers from the patients, in order to present patient specific information in different graphs. Data from different questions should be grouped together to visualize important relationships and correlations between variables. Graphs should be constructed to show development over time for chosen variables.
Calculations on the collected and non-collected data, which should trigger reminders to the patients about continuously answering the questions.
Algorithms enabling the question schedules.
Applications handling and securing that patient specific information should only be viewed by authorized personnel.
Applications handling and securing that feedback should be realized in different digital channels such as Internet and messages.

Figure 4A:
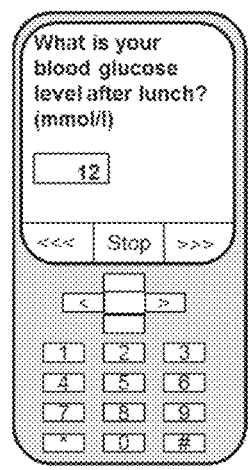
FIGS. 4A-4C illustrate examples of question presented in the mobile phone and example of feedback. (4A) Numeric question; (4B) Feedback graphs with patient specific data; (4C) Feedback graphs with patient specific data, user interface on a regular computer.
Figure 4B:
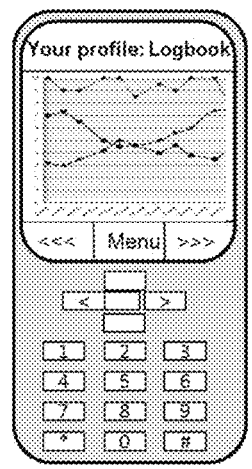
Figure 4C:
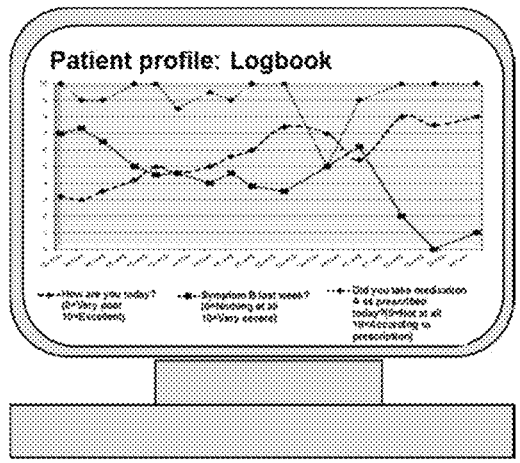

Patient-specific feedback information (see FIGS. 4A-4C). Some of the characteristics:
Should be developed based on the specific aspects of the PP: s and the patient category.
Patient specific graphs based upon the collected answers from the patients to the set of questions. Health care personnel should have access to these patient specific graphs, which they should use for giving feedback in different ways to the patients.
The graphs should be constructed in a way where relevant variables are matched together and plotted over time according to the set of functions. This should show interesting and valuable relationships and correlations that will give both the patients and/or the healthcare personnel a better understanding of the patients' situation and development.
Patient specific messages sent to the patients regarding their treatment and situation.
Patient specific messages sent to the patients with reminders to continue answering questions when their adherence to answer the questions have decreased or stopped.
Oral communication between health care personnel and the patients based on the patient specific feedback information generated by the CPP.

Figure 5:
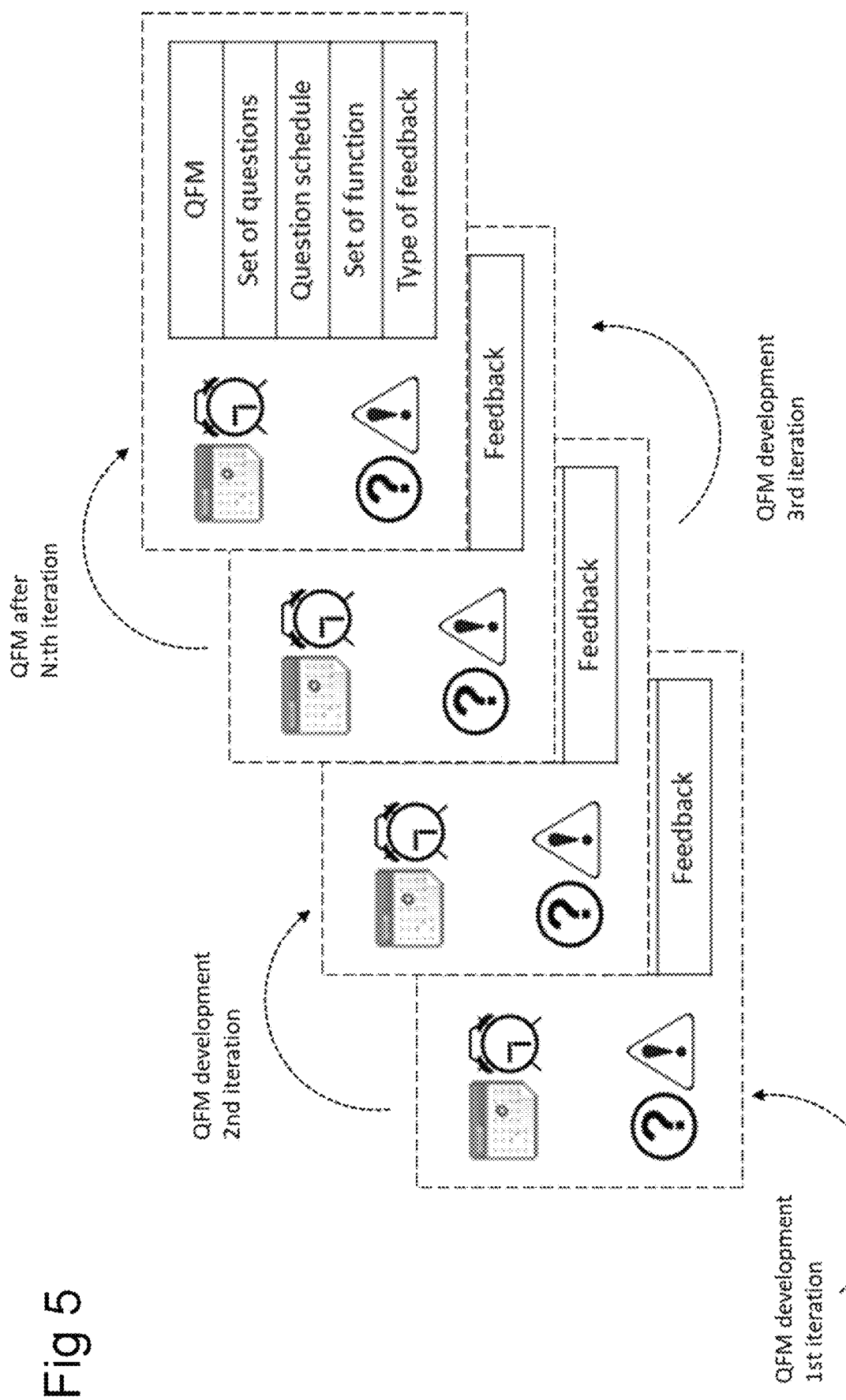
FIG. 5—Development of the model
Figure 6:
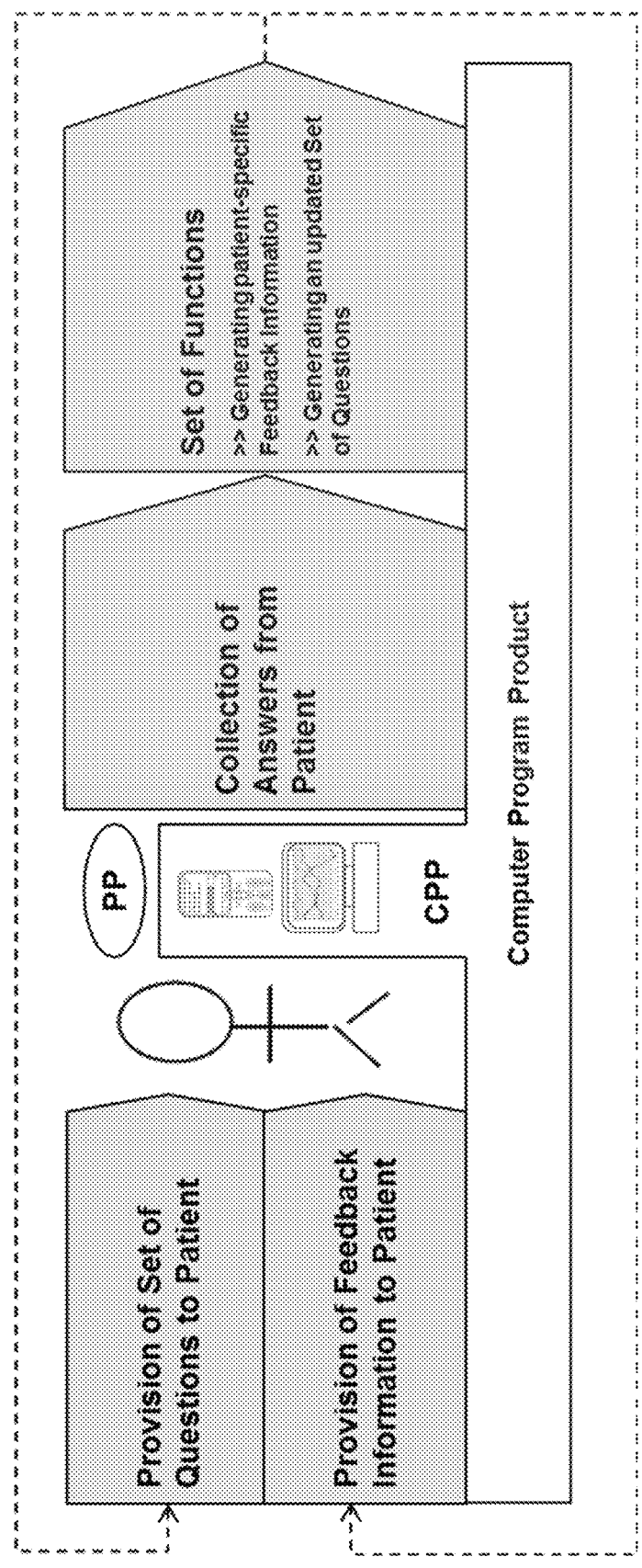
FIG. 6—Overview embodiment of the model in the study
Figure 7:
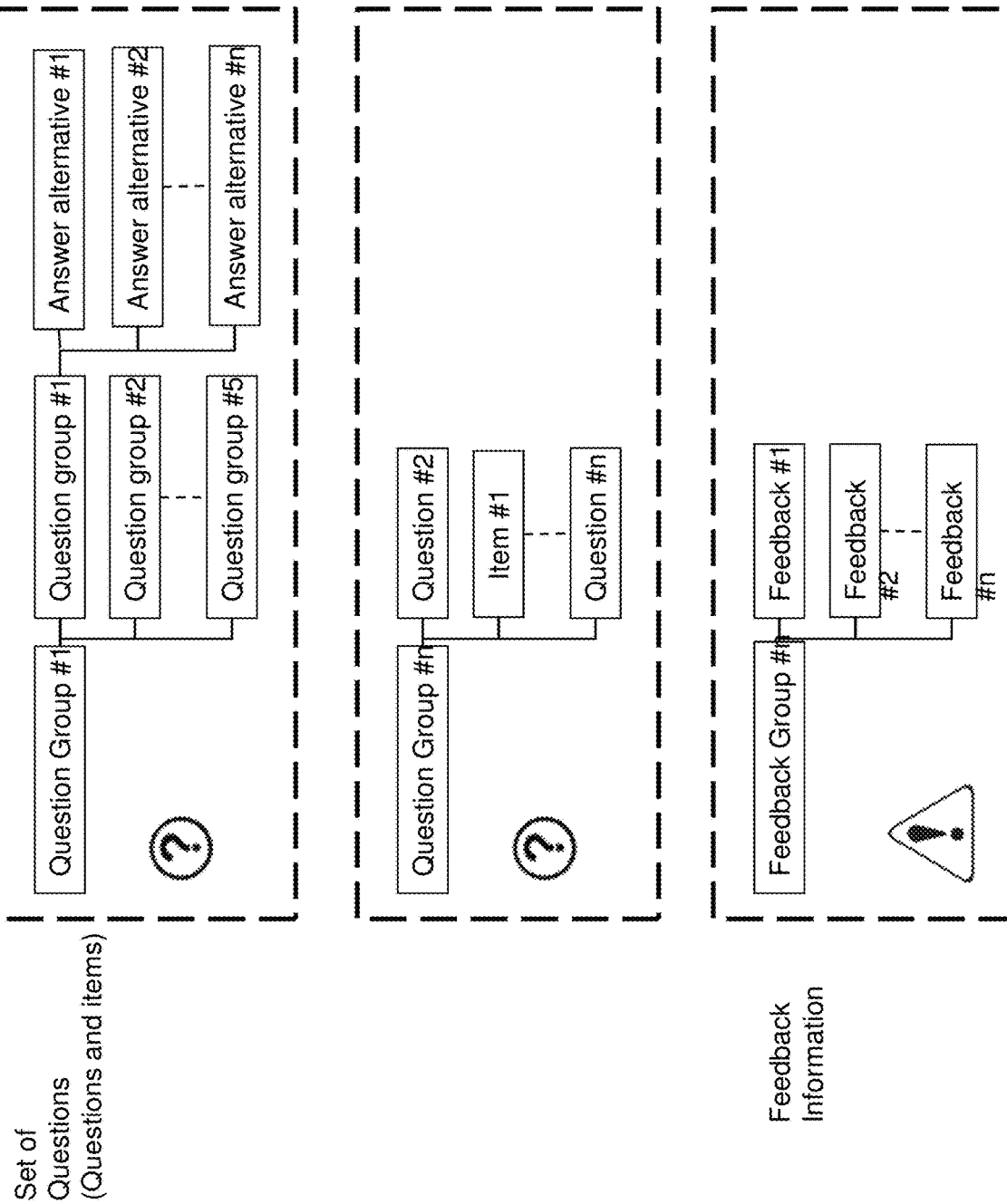
FIG. 7—Schematic view of Set of Questions and Feedback Information
Figure 8:
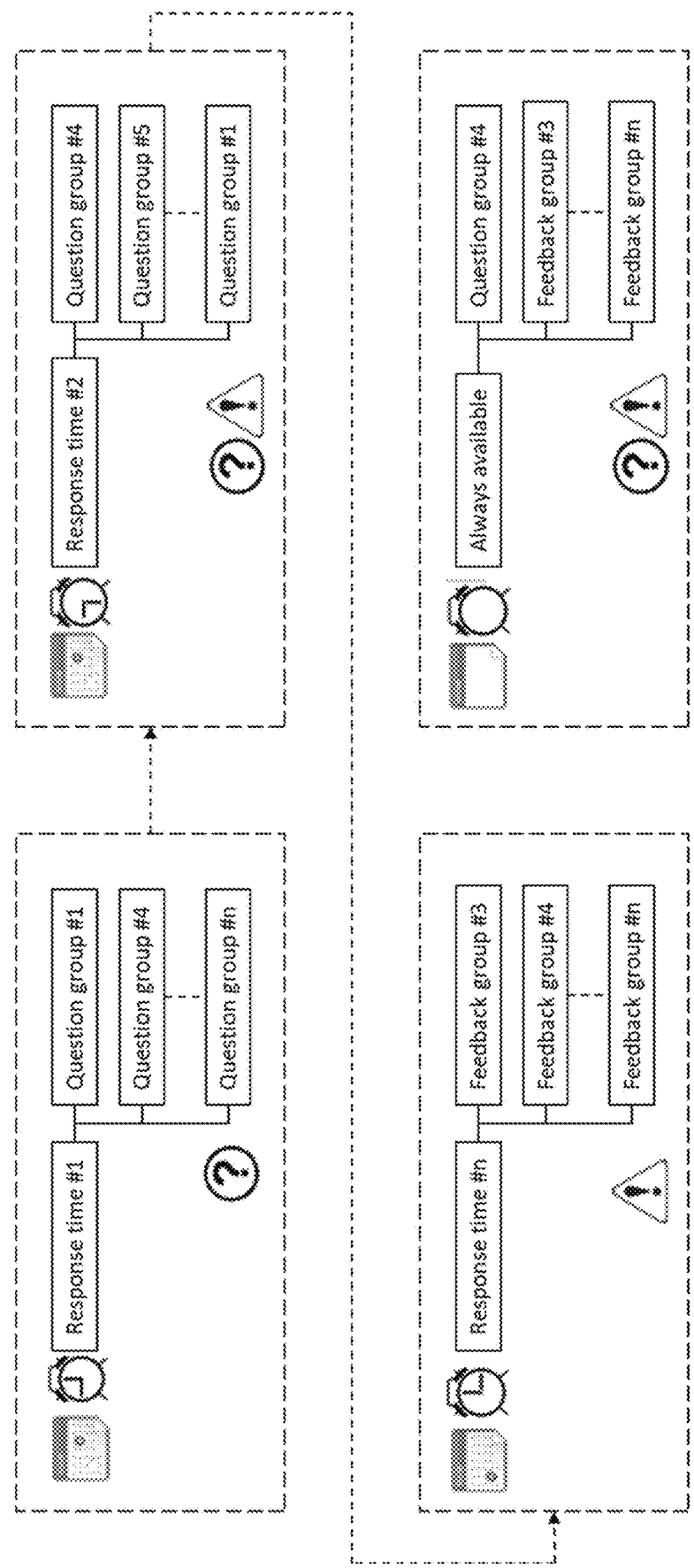
FIG. 8—Schematic view of the question schedules

The development of the used model (QAFM and QFM) for the PP:s in the study should include mainly the steps described earlier in the detailed description and clinically relevant information of the specific PP:s and the patient category. It is an iterative process (see FIG. 5) before optimal models for the specific PP:s (see FIG. 6) have been developed with the set of questions and feedback information (see FIG. 7) and the question schedules (see FIG. 8). As said earlier in the detailed description, many aspects and considerations need to be taken into account when developing the specific model.

Overview Technical Implementation of the CPP

Figure 9:
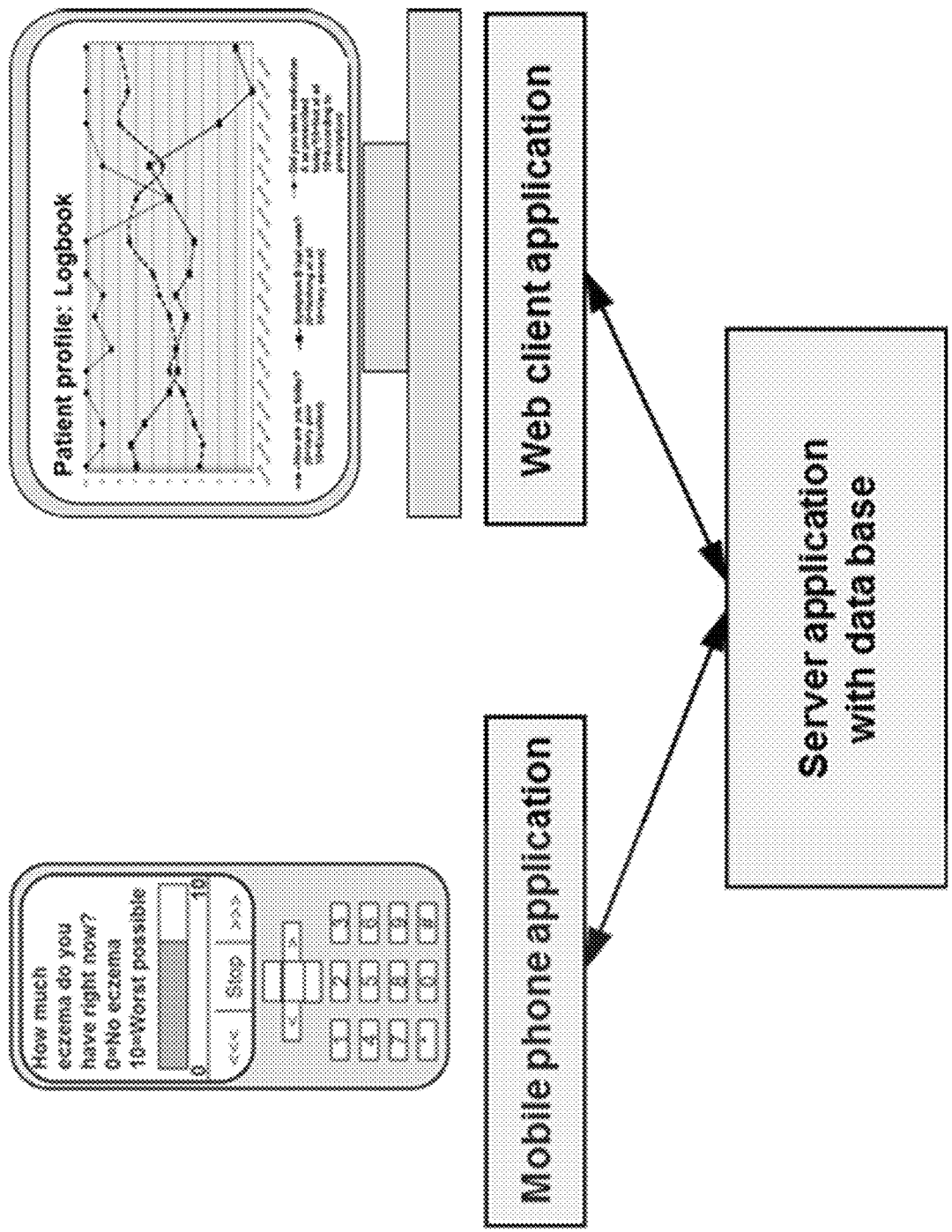
FIG. 9—Overview technical implementation of the CPP

The technical realization and implementation of the CPP in the study is illustrated in FIG. 9. The patients should first be registered in the system by the health care personnel and after that the patients should download, via mobile internet, the mobile phone application to their mobile phones. The mobile phone application will process, handle and present the questions and answers to the patient. The CPP will also consist of a web client application which has the primary user interface for the health care personnel. A server application with a data base will also be an integral part of the implementation of the CPP.

Diabetes is an auto-immune disease in which the body's immune system destroys the insulin-producing beta cells in the pancreas. This type of diabetes, also known as juvenile-onset or insulin-dependent diabetes, accounts for 10-15% of all people with the disease. People with type 1 diabetes must inject themselves with insulin several times a day and follow a careful diet and exercise plan.

Glycated hemoglobin (hemoglobin A1c, HbA1c, A1C) is a form of hemoglobin that is measured primarily to identify the average plasma glucose concentration over prolonged periods of time. This serves as a marker for average blood glucose levels over the previous months prior to the measurement.

HbA1c is recommended by WHO (World Health Organization) as a test to diagnose diabetes. The American Diabetes Association recommends that the HbA1c should be below 53 mmol/mol (7.0%) for most patients.

Rapid-acting insulin begins working very quickly inside the body—usually within 5 and 10 minutes. This type of insulin should be taken just before or just after eating. It operates at maximum strength for one to two hours and duration is typically up to four hours. Rapid-acting insulin's are very convenient because they allow diabetic patients to inject themselves, at the time, when they eat. Long-acting insulin should be taken once a day at the same time each day to lower the blood glucose.

The study objective is to evaluate the clinical effect of using the combination product, the two PP:s and a CPP, in type1 diabetes in comparison of using only the stand-alone PP:s themselves. The measured variable should be HbA1c. The variable should be measured directly before the patients entered into the study and directly afterwards when they had concluded their participation.

The patients in the intervention group should be given the combination product, meanwhile the patients in the control group will be given only the separate PP:s.

Primary variable: HbA1c.

Length of study: 6 months

Number of patients: 20 in the intervention group and 20 in the control group Inclusion criteria: Diagnosed diabetes type1 with more than 53 mmol/mol HbA1c. Access to a mobile phone capable of handling the used CPP.

Used PP:s: Rapid-acting insulin; Apidra and a long-acting insulin; Lantus

The used set of questions can be seen in table 1. The different questions were grouped together in questions groups with corresponding response times (see table 2). Some of the questions were asked three times a week, some more seldom, and some were "spontaneous", i.e., always available for the patient to answer. The question regime, appeared to the patient, could be another than the one presented in the table.

The set of questions for the QAFM is to be the following: 1-5, 8-16, 20-23

The set of questions for the QFM of Apidra (the first PP) is to be the following: 6, 7

The set of questions for the QFM of Lantus (the second PP) is to be the following: 17-19

TABLE 1

| Questions | |
|---|---|
| Question | Question type and answer alternatives |
| 1. "Have you been irritated at someone/something today?" | VAS 0-10<br>0 = Not at all irritated, 10 = Extremely irritated |
| 2. "How focused are you at school/work?" | VAS 0-10<br>0 = Not at all focused, 10 = Very focused |
| 3. "How did you sleep last night?" | VAS 0-10; 0 = Very poorly, 10 = Very well |
| 4. "For how long time have you exercised today?" | Multiple choice: 0 min, 1-20 min, 21-40 min, 41-60 min, More than 60 min |
| 5. "How many blood glucose levels have you checked today?" | Numeric |
| 6. "How many units of Apidra did you take at breakfast?" | Numeric |
| 7. "How many units of Apidra did you take at the meal?" | Numeric |
| 8. "When did you eat breakfast?" | Multiple choice: Before 6 am, Between 6-8 am, Between 8-10 am, I didn't eat breakfast |
| 9. "When did you eat lunch?" | Multiple choice: Before 11 am, Between 11 am-1 pm, Between 1-3 pm, I didn't eat lunch |
| 10. "When did you have dinner?" | Multiple choice: Before 5 pm, Between 5-7 pm, Between 7-9 pm, I didn't eat dinner |
| 11. "What was your blood glucose level approximately 1.5 hours after breakfast (mmol/l)?" | Numeric |

TABLE 1-continued

Questions

| Question | Question type and answer alternatives |
|---|---|
| 12. "What was your blood glucose level approximately 1.5 hours after lunch (mmol/l)?" | Numeric |
| 13. "What was your blood glucose level approximately 1.5 hours after dinner (mmol/l)?" | Numeric |
| 14. "What was your blood glucose level before breakfast (mmol/l)?" | Numeric |
| 15. "What was your blood glucose level before lunch (mmol/l)?" | Numeric |
| 16. "What was your blood glucose level before dinner (mmol/l)?" | Numeric |
| 17. "Did you take your Lantus today?" | Multiple choice: Yes, No, Probably, Probably not |
| 18. "How many units of Lantus did you take today?" | Numeric |
| 19. "At what time did you take your Lantus?" | Numeric |
| 20. "How do you feel?" | VAS 0-10; 0 = Extremely bad, 10 = Extremely good) |
| 21. "Your weight this morning?" | Numeric |
| 22. "How hard is it to have been diagnosed with type1 diabetes?" | VAS 0-10; 0 = Not at all difficult, 10 = Extremely hard |
| 23. "To what extent has diabetes affected your activities during the week?" | VAS 0-10; 0 = Very much, 10 = Not at all |

TABLE 2

Question schedule

| Question group | Response time (alerts from CPP) |
|---|---|
| "Morning questions" | Mondays and Thursdays at 10 am |
| "Afternoon questions" | Mondays and Thursdays at 3 pm |
| "Evening questions" | Mondays and Thursdays at 9 pm |
| "Weekly questions" | Once a week on Fridays at 3 pm |
| "Monthly questions" | Once a month on Fridays at 3 pm |
| "Spontaneous questions" | Questions always available to answer |

The feedback to the patients is crucial in order to achieve a positive clinical effect of the combination product.

Figure 10:
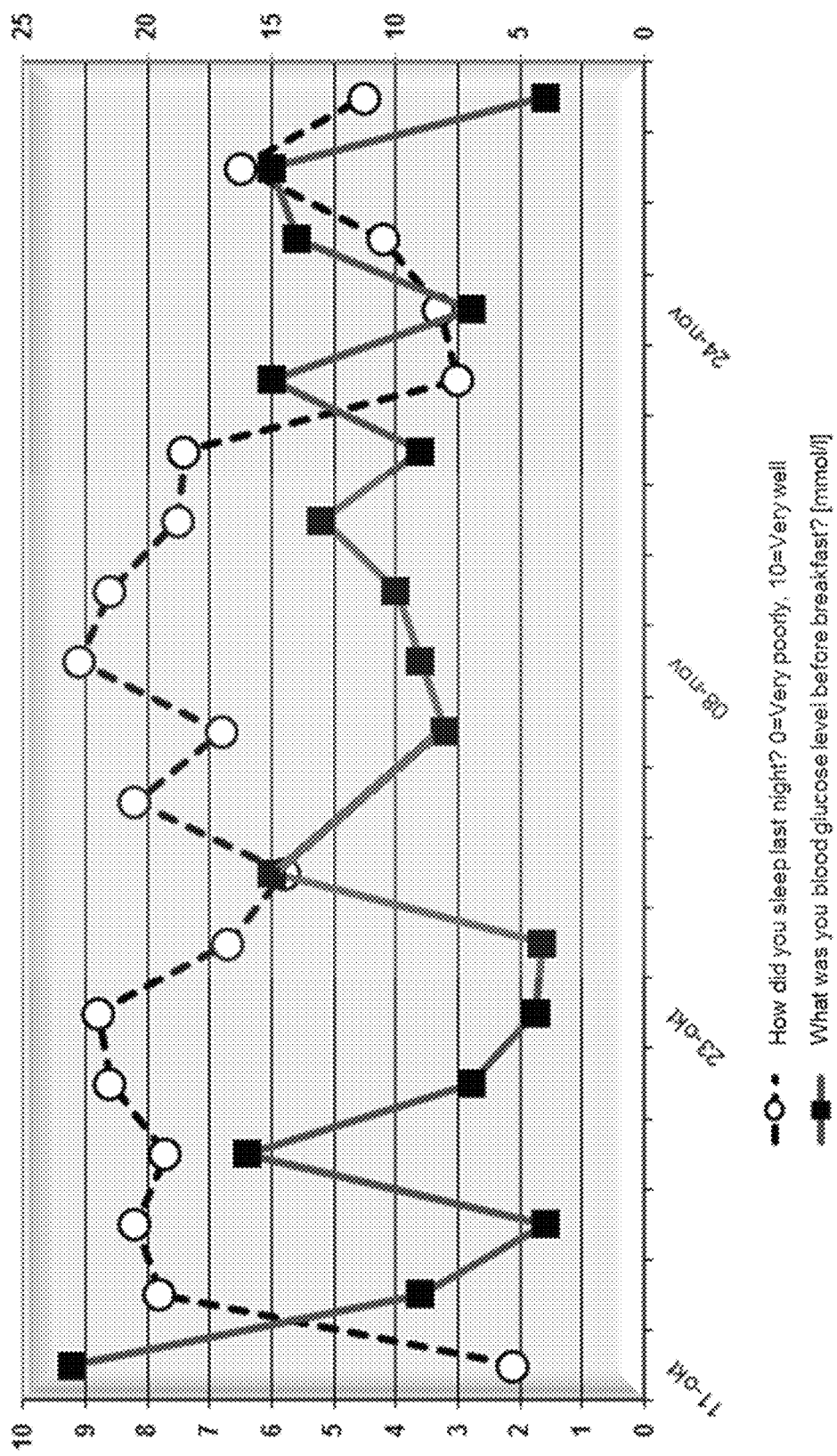
FIG. 10—Example of a possible patient feedback graph

Both the healthcare personnel and the patients should have access to updated graphs with the patient's specific feedback information based on the collected answers. The graphs are constructed in a way where relevant variables are matched together and plotted over time, examples of matched variables are shown in table 3. An illustrative example of a possible patient's possible feedback graph is shown in FIG. 10. Examples of possible feedbacks that could be given to the patients are presented in table 4.

TABLE 3

Examples of grouping of variables in feedback graphs

| Grouping of feedback graphs | Questions/Variables |
|---|---|
| Blood glucose and insulin at breakfast | "What was your blood glucose level before breakfast (mmol/l)?" "How many units of rapid-acting insulin did you take at breakfast?" "What was your blood glucose level approximately 1.5 hours after breakfast (mmol/l)?" |
| Sleep and blood glucose | "How did you sleep last night?" "What was your blood glucose level before breakfast (mmol/l)?" |

In the following, two patient studies are described (one performed and one prospective). In the patient cases a combination product of two or more pharmaceutical products integrated with a mobile software application, respectively adapted specific QFM:s and QAFM to the pharmaceuticals, were used. For one of the combination products a study was performed, for the other the study is prospective. In the study which was performed, there was a period as well when the patient was using some of the pharmaceuticals solely without the integration of the mobile software application and the specifically adapted QFM:s and QAFM.

The examples showed the necessity to adapt the set of functions given the specific capabilities for the pharmaceuticals, such as different levels of adherence and adverse events; and whether it is critical or not to warn the patient for particular registrations of a variable.

Study 2: Development of Combination Product Based on Brilique and ASA Introduction Development of a combination product based on the pharmaceuticals Brilique and acetylsalicylic acid (ASA), specifically adapted QFM:s and QAFM with a dependent software application
   a. Test objectives; improved cardiovascular symptoms measured as level of mortality
   b. Main intervention factors;
      i. an improved administration and adherence of Brilique
      ii. an improved adherence to ASA
      iii. an improved level of physical activity
   c. Follow-up variables: Level of mortality, adherence to Brilique and amount of physical activity
   d. Period of time using the combination product: None; is to be initiated. This is an example of a combination product and a possible test to prove the effect of the invention.

Set of Questions Brilique and ASA

The used set of questions for the specific QFM:s and QAFM in the combination product based on Brilique and ASA is the following:
   Adherence to
      Brilique; The patient will be asked to answer a question whether or not he/she will be adherent to Brilique; "I have taken my Brilique this morning/this afternoon". This question will show up once a day in the software application. No questions regarding dose will be given.

ASA; The patient will be asked to answer a question whether or not he/she will be adherent to ASA; "I have taken my ASA today". This question will show up once a day in the software application. No questions regarding dose will be given.

Physical activity;

The patient will be asked initially to set up an individual goal with the purpose of achieving an increased effect which is possible to update during a test. The individual goal will be set-up by the patient by answering the following question: "Give your own personal goal for the physical activity in number of minutes for one week". The patient will then be asked to continuously answer a question like the following: "I have been exercising the following number of minutes today: [number]", as well.

Weight/BMI;

The patient will be asked to answer a question regarding his/her actual weight.

Blood pressure;

The patient will be asked to measure his/her actual blood pressure, either by himself/herself at home or at a clinic. Afterwards he/she is able to register it in the software application by answering a question concerning both the systolic and diastolic pressure, and where he/she had measured it; at home or at a clinic. It is possible for the patient to change or update such already registered answers.

Blood glucose;

The patient will be asked to register the measured blood glucose, if he/she has measured it. It is possible for the patient to change or update such already registered answers.

HbA1c;

The patient will be asked to register the HbA1c after it has been measured at a clinic. For the defined set of questions adherence to Brilique, adherence to ASA, physical activity and weight/BMI will be prioritized in order to gain effect for the patient. The prioritization implies that the feedback messages and also the visual feedback will be focused on these questions, resulting in higher frequency of showing them, and the visual feedback will be prominent compared to the other questions.

Set of Functions Brilique and ASA

The set of functions for adherence to Brilique and to ASA, and the related type of feedback, will be defined according to the following logic:

1. At a level
    Brilique: of more than 85% of the tablets of Brilique has been taken during the last week, where the normally ordinated amount of tablet per week is fourteen, implying that no more than two missed tablets was missed, the patient shall be given a green color of the visual feedback since he/she will be regarded as adherent. In addition to that the missed tablets must not be in a row, causing a gap, in order for the patient to be regarded as adherent. Feedback messages encouraging the patient to remain adherent shall be given.
    ASA: defined as a maximum of totally one missed occasion the last week, a general type of feedback message will be shown to the patient indicating he/she is adherent. The patient will also be given a green color on the visual feedback.
2. At a level
    Brilique: of below 85%, but above 70% of the tablets of Brilique has been taken the last week, in addition to that the maximum missed tablets in a row was two, the patient shall be given a yellow color of the visual feedback. Feedback messages encouraging the patient to increase the level of adherence to Brilique shall be given, but they shall not be critical.
    ASA: defined as of two or three missed tablets the last week, the patient will be regarded as non-adherent but not critical. Another type of message will be shown to the patient. The patient will be given a yellow color on the visual feedback.
3. At a level
    Brilique: of less than 50% of the tablets of Brilique has been taken during the last week, or if the amount of missed tablets in a row was three or more, the patient shall be given a red color of the visual feedback. Feedback messages encouraging the patient to promptly increase the level of adherence to Brilique shall be given, since the situation may be critical.
    ASA: defined as four or more missed tablets last week, the patient will be regarded as non-adherent and critical. Another type of message will be shown to the patient. The patient will be given a red color on the visual feedback.

The set of functions for physical activity are utilizing both personal and official goals, based upon the following structure:

1. The use of individual goals or not
2. The patient reaches his/her individual goal or not
3. The patient reaches his/her formal objectives or not
4. A mix of point two and three The personal goal can, for the Brilique QFM, be defined as zero since some patients are ordinated not to be physically active during the first treatment period. After a period of time, the healthcare personnel may update the goal to normal levels.

The patient will be shown feedback messages depending on which of the above levels he/she has registered.

For weight/BMI feedback messages will be shown every second week depending on which of the following BMI levels the patient recently has registered during the last two weeks:

1. BMI between 20 and 25
2. BMI between 25 and 30
3. BMI between 30 and 35
4. BMI above 35

If the patient will have registered either a clearly decreasing or increasing trend of the BMI, the patient will be given messages concerning the purpose of either maintaining the trend or trying to interrupt it.

When the total number of patients in the test is exceeding one hundred, a change in frequency and type of messages for adherence to Brilique is performed. For patient one hundred one up to patient two hundred, the frequency of the given adherence messages will be lowered and the type of messages will be a bit friendlier.

When the total number of patients in the test is exceeding two hundred, an evaluation concerning the frequency and type of given feedback messages for adherence will be performed by the set of functions. The result of the level of adherence for the first hundred patients will be compared to the result of the second hundreds of patients. If the first hundred patients are more adherent to Brilique concerning the actual period of green status for the patients, than the others, the frequency of given adherence messages will be as the used frequency for the first hundred patient. If the second hundred patients are more adherent, frequency for the first hundred will be increased. The similar evaluation is done concerning the level of friendliness in the messages.

When the total number of patients in the test is exceeding three hundred, a similar evaluation concerning adherence optimization is performed but in the opposite direction—given that the first hundred patients were most adherent—i.e. the evaluated frequency for new patients will be higher, i.e. more frequent, and the level of friendliness in the messages will be lower. If the second hundred patients were the most adherent in the first place, this evaluation will instead be against an even lower frequency and more friendly messages.

Corresponding evaluations is then performed, also decoupling the level of frequency and the level of friendliness in the messages, in order to optimize the level of adherence to Brilique among the patients using the combination product. When the number of patients is exceeding five hundred a similar evaluation is performed concerning the illustration of the visual graph for the type of feedback for adherence, where different types of illustrations are compared to each other in order to optimize the level of adherence.

Similar evaluations, in order to optimize adherence, is performed regarding ASA. However, there will be no evaluations concerning the illustration of the visual graph for the type of feedback for adherence to ASA. Instead, the illustrations will be evaluated and changed strictly according to the Brilique evaluation.

When the total number of patients in the test is exceeding two hundred, the $65^{th}$ percentile of the registered average values of performed level of physical activity from this population, will be used as the official objective for physical activity instead of the original set-up value. For every new patient this official objective will continuously be updated in order to achieve a proper objective.

When the total number of patients in the test is exceeding five hundred, the official objective for physical activity will be structured, as well, according to separate objectives for each month, based on the performed registrations from patients in the test, starting from the initiation of using the combination product. Hence, the official objective for physical activity will most probably be different for each month for the new patients using the combination product.

When the total number of patients in the test is exceeding one thousand, the official objectives for physical activity will be structured, as well, according to separate objectives for each week, based on the performed registrations from patients in the test, starting from the initiation of using the combination product. Hence, the official objective for physical activity will most probably be different for each week for the new patients using the combination product.

Type of Feedback Brilique and ASA

The following feedback components, controlled by the set of functions, will be given to the patient:

Individual, predefined messages to be shown in the software application in the patient's mobile phone. The total amount of messages may exceed two hundred-fifty. They are all kindly designed.

A simple, illustrative individual graph per variable, showing the registrations of the patient in relation to personal and official objectives. Different amount of information will be shown for different variables.

An image/symbol indicating the actual level for the health status of each variable, illustrated as a circle with different colors and numbers within, will be shown for the prioritized variables.

A table showing an amount of the latest registrations will be shown in the view of the variable. From this table some of the variable registrations will be possible to update.

Reminders, which the patient will be given when he/she has forgotten to register whether he/she has been adherent to the specific pharmaceutical or not.

General, static information without any relation to given answers from the patient. This contains information about the disease, the symptoms and the treatment.

The feedback to the patient will be immediate in the sense that also the latest registration will be able to affect the set of functions. This set-up will be verified in a small initial test prior to the example as important for achieving clinical effect, especially for the visual type of feedback.

An example of a feedback message for a patient with a green status regarding adherence to Brilique is: "It's good that you are taking Brilique as agreed upon with your doctor. By doing so you are decreasing the risk for getting a heart attack." Corresponding messages will be shown for adherence to ASA.

A visual graph illustrating the patient adherence to Brilique and to ASA the last week will be showing a diagram with twenty-one different symbols for the actual seven days, fourteen for Brilique and seven for ASA, since the patient shall take Brilique twice and ASA once a day. If the patient doesn't answer the question whether he/she has taken the specific pharmaceutical for a specific occasion, a red cross will be shown. If the patient will register that he/she took the pharmaceutical, a green tick is shown instead.

An example of an individual message for physical activity when the patient has fulfilled both the personal and official objectives is: "Good job! By remaining at this level of physical activity, which you are at now, a longer period of time you will substantially decrease the risk of getting another heart disease." The patient will be given feedback messages for physical activity with a similar frequency to the patient as for adherence to Brilique and ASA. A visual graph showing the actual achieved amount of physical activity per week the last month, for the patient will be shown in the software application. It is illustrated through different staples in relation to both the personal goal and the official goal of the amount of physical activity.

Depending on the actual BMI level individual feedback messages shall be shown. Focus on the information in the messages is on food intake. An example of a message to a patient with BMI above 35 is: "Proper eating habits are a central part of your treatment since you have a risk for heart disease."

A visual graph will be shown indicating the patient's actual BMI level, and in the background of the graph different colors with green for BMI less than 25; light yellow for BMI above 25 and less than 30; darker yellow for BMI above 30 and less than 35; light red for BMI above 35.

For blood pressure, blood glucose and HbA1c only general feedback messages will be given to the patient without relation in the set of functions to the actual registered patient values. The messages will be focusing on general health, such as physical activity and food intake, but also mention blood pressure, blood glucose and HbA1c in order to make the patient aware of them. For the three variables visual graphs are to be shown for the actually registered patient values.

Since the test is to be initiated, no results exist at this very moment.

Study 3: Development and Test of Combination Product Based on Zoloft, Metformin and Januvia Introduction Development and test of a combination product based on Zoloft, Metformin and Januvia, their respectively specifically adapted QFM:s the QAFM and dependent software application a. Test objectives; improve cardiovascular and diabetes symptoms
b. Main intervention factors;
 i. Improved administration and adherence of Zoloft
 ii. Improved administration and adherence of Metformin
 iii. Improved adherence to Januvia
 iv. increased well-being initiating an improved level of physical activity
c. Follow-up variables: Weight and HbA1c
d. Period of time using the combination product: Five months.
e. Period of time using only two of the pharmaceuticals, i.e. no combination product, prior to the period of using the combination product: Four months Set of Questions Zoloft, Metformin and Januvia The used set of questions within the specific QFM:s and QAFM in the combination product based on Zoloft, Metformin and Januvia was the following:

Adherence to all of the three pharmaceuticals. The patient was asked to answer questions whether or not he/she has been adherent to:
 Zoloft, and which dose the patient had taken; "I have taken my Zoloft today with the dose 25 mg/50 mg/100 mg/150 mg or 200 mg".
 Metformin, and which dose the patient took; "I have taken my Metformin today with the daily dose of 500 mg/1000 mg/1500 mg/2000 mg/2500 mg or 3000 mg".
 Januvia; "I have taken my Januvia today".

Physical activity:

The patient was asked initially to set up an individual goal with the purpose of achieving an increased effect. The individual goal was set-up by the patient by answering the following question: "Give your own personal goal for the physical activity in number of minutes for one week".

The patient was then asked to continuously answer a question like the following: "I have been exercising the following number of minutes today: [number]".

Weight/BMI;

The patient was asked to answer a question regarding their actual weight.

Blood glucose;

The patient was asked to register their measured blood glucose, when he/she had measured it. It was possible for the patient to change or update already registered answers.

HbA1c;

The patient was asked to register their HbA1c after it has been measured at a clinic.

Depression and Anxiety, respectively;

The patient was asked to register the actual level of perceived depression respectively actual level of perceived anxiety at predefined occasions every second day. It was also possible for the patient to answer the question when he/she wanted. The questions were structured as a Visual Analog Scale (VAS).

Stress;

The patient was asked to register the actual level of perceived stress. The question did show up at predefined occasions every second day. It was also possible for the patient to answer the question when he/she wanted. The question was structured as a VAS.

Three specific possible adverse events for Zoloft:
 "Do you have severe skin rash in your mouth or tongue? Extremely skin rash versus No skin rash at all" according to a Visual Analogue Scale
 "Do you experience symptoms such as itchy rash, respiratory problems, wheezing or swellings in your face? Extremely much versus Nothing at all" according to a VAS structure
 "Have you been upset or confused; or had diarrhea, fever and high blood pressure; or had excessive sweating and rapid heartbeat? Extremely much versus Nothing at all" according to a VAS structure A possible adverse event for Metformin;
 "Have you experienced unexpected loss of weight, severe nausea or vomiting (malaise), uncontrolled sudden pain when breathing or abdominal? Extremely much versus Nothing at all" according to a VAS structure A possible side effect for Metformin;
 "Have you experienced diarrhea, decreased appetite, malaise or abdominal pain particularly during the initial treatment? Extremely much versus Nothing at all" according to a VAS structure Two possible adverse events for Januvia;
 "Have you experienced severe and persistent abdominal pain? Extremely much versus Nothing at all" according to a VAS structure
 "Have you experienced a severe allergic reaction, such as rash, hives, and swelling of the face, lips, tongue and throat which could cause breathing or swallowing difficulties? Extremely much versus Nothing at all" according to a VAS structure All of the questions were equally prioritized, in order to gain effect for the patent, except for HbA1c, Anxiety and Stress, the adverse events and side effects. The prioritization implied that the feedback messages and also the visual feedback were focused on these questions, resulting in higher frequency of showing them, and the visual feedback was prominent compared to the other questions.

Set of Functions Zoloft, Metformin and Januvia

The set of functions for adherence to all of the three pharmaceuticals Zoloft, Metformin and Januvia, and the related type of feedback, was defined according to the following logic. One occasion for Metformin was defined as a daily dose.

1. At a level
 a. Zoloft: defined as a period of only one missed occasion, or less, to take tablet(s), i.e. not two missed occasions, or more, taking tablets in a row, a general type of feedback messages was shown to the patient every third day indicating he/she was adherent. The patient was also given a green color on the visual feedback.
 b. Metformin: defined as a period of only one missed occasion, or less, to take tablet(s), i.e. not two missed occasions, or more, taking tablets in a row, and a maximum of totally two missed occasions a week, a general type of feedback message was shown to the patient every third day indicating he/she was adherent. The patient was also given a green color on the visual feedback.

c. Januvia: defined as a maximum of totally one missed tablet the last week, a general type of feedback message was shown to the patient every third day indicating he/she was adherent. The patient was also given a green color on the visual feedback.

2. At a level
   a. Zoloft: of two missed occasions to take tablets, or more, in a row, the patient was regarded as non-adherent. Another type of message was shown to the patient every third day. The patient was given a red color on the visual feedback.
   b. Metformin: defined as a period of maximum of two missed occasions to take tablets in a row, or three missed occasions the last week, the patient was regarded as non-adherent but not critical. Another type of message was shown to the patient every third day. The patient was given a yellow color on the visual feedback.
   c. Januvia: defined as of two or three missed tablets the last week, the patient was regarded as non-adherent but not critical. Another type of message was shown to the patient every third day. The patient was given a yellow color on the visual feedback.

3. At a level
   a. Zoloft: (Nothing)
   b. Metformin: defined as a period of three missed occasions to take tablets in a row or more, or totally four or more missed occasions the last week, the patient was regarded as non-adherent and critical. Another type of message was shown to the patient every third day. The patient was given a red color on the visual feedback.
   c. Januvia: defined as four or more missed tablets last week, the patient was regarded as non-adherent and critical. Another type of message was shown to the patient every third day. The patient was given a red color on the visual feedback.

The set of functions for physical activity was utilizing both personal and official goals. The personal goal was able to update by the patient whenever he/she wanted. The physical activity official goal was higher than for both Brilique and only using Zoloft.

The patient was given feedback messages for physical activity using the following structure:
1. The use of individual goals or not
2. The patient reaches their individual goal or not
3. The patient reaches their official goal or not The patient was given individual feedback messages depending on which of the above levels he/she registered.

For weight/BMI feedback messages were sent dependent on which of the following BMI levels the patient recently had registered during the last two weeks:
1. BMI between 20 and 25
2. BMI between 25 and 30
3. BMI between 30 and 35
4. BMI above 35

Set of functions for Blood glucose, connected to the blood glucose question, was configured to detect possible hyperglycemia and/or hypoglycemia for the patient. A predefined amount of registrations above a defined level for hyperglycemia or below another for hypoglycemia triggered predefined messages.

If the patient registered blood glucose three times in a row exceeding 15 mmol/L messages for hyperglycemia were shown to the patient and registrations at only one occasion below 2.5 mmol/L a message for hypoglycemia was shown.

Set of functions for both Depression and Anxiety was configured to detect a predefined amount of registrations above a certain level of the variable performed during a specific time interval; at least three registrations above the level eight during at least three days. When that criterion was fulfilled a predefined message was shown to the patient.

Set of functions for Stress and HbA1c didn't cause any feedback to the patient.

Set of functions for the possible adverse events for Zoloft and Metformin was according to the following logic:
1. If any of the questions resulted in a registration on the VAS exceeding level five on the ten grade scale, a message was shown to the patient that he/she should contact his/her responsible doctor and describe his/her situation
2. If any of the questions resulted in a registration on the VAS exceeding level seven on the ten grade scale, a message was shown to the patient that he/she should promptly contact his/her responsible doctor and describe his/her situation Set of functions for the possible adverse events for Januvia was according to the following logic:
1. If any of the two questions resulted in totally three performed registrations on the VAS exceeding level four on the ten grade scale, a message was shown to the patient that he/she should contact his/her responsible doctor and describe his/her situation
2. If any of the questions resulted in a registration on the VAS exceeding level six on the ten grade scale, a message was shown to the patient that he/she should promptly contact his/her responsible doctor and describe his/her situation Set of functions for the side effect for Metformin was according to the following step:
1. If the question resulted in a registration on the VAS exceeding level seven on the ten grade scale, a message was shown to the patient that he/she should contact his/her responsible doctor and describe the situation Type of Feedback Zoloft, Metformin and Januvia The following feedback components, controlled by the set of functions, were given to the patients:

Individual, predefined messages shown in the software application in the patient's mobile phone. The amount of messages exceeded hundred and they were all kindly designed.

A simple, illustrative individual graph per variable, showing the patient's registrations in relation to personal and official objectives for the actual pharmaceuticals. The time scales differed between the different variables.

An image/symbol indicating the actual level for the health status of each prioritized variable, illustrated as a circle with different colors and numbers within, were shown for the prioritized variables.

General, static information without any relation to given answers from the patient.

The feedback to the patient was immediate in the sense that also the latest registration should be able to affect the set of functions.

An example of a feedback message to the patient with a green status on adherence to Metformin was: "It's good that you are taking Metformin according to prescription. By doing so you are improving your situation with diabetes".

An example of an adherence message with red status was: "You shouldn't miss taking Metformin, it would help you with your diabetes"

An example of feedback message to the patient with a green status on adherence to Januvia was: "Last week you have been taking Januvia completely according to your ordination—Good!" Corresponding messages were used as well for Zoloft.

A visual graph illustrating the patient adherence to Zoloft, Metformin and Januvia the last week showed a diagram with twenty-one different symbols for the actual seven days, three for each day the patient is supposed to take the daily dose for the respective pharmaceutical. If the patient didn't answer the question whether he/she had taken the specific pharmaceutical for a day, or denied to take it, a red cross was shown for the actual pharmaceutical. If the patient had registered that he/she took the pharmaceutical, a green tick was shown instead in the diagram.

The patient was given feedback messages depending on which of the levels of physical activity he/she registered. An example of a message when the patient has reached the official goal: "Really good job with your exercise! By being physically active your heart will be more powerful and you will absolutely feel better". Corresponding messages were also shown if the patient reached their personal goal, but since the official goal was relatively high, the most positive messages were given for that.

A visual graph showing the actual achieved amount of physical activity per week, for the last two months, was shown in the software application. It was illustrated through different staples in relation both to the personal goal and to the official goal of amount of physical activity. Depending on the actual BMI level feedback messages were shown. Focus on the information in the messages was food and physical activity. An example of a message sent to a patient with BMI above 35 was: "By losing weight you will get several positive effects such as improved blood glucose control, reduced lipids and decreased blood pressure."

A visual graph was shown indicating the patient's actual BMI level, and in the background of the graph different colors with green for BMI less than 25; light yellow for BMI above 25 and less than 30; darker yellow for BMI above 30 and less than 35; light red for BMI above 35. When the set of functions triggered a condition of hyperglycemia for the patient, a corresponding message was shown: "You seem to have had a little too high value on blood glucose. Hence, think of both being adherent to Metformin and having a proper intake of energy. If you have any questions, you could contact your responsible doctor".

When the set of functions triggered a condition of hypoglycemia, a corresponding message could be shown: "You seem to have low blood sugar. If you haven't already done it you should immediately take some sugar. If this frequently happens you should contact your responsible doctor".

HbA1c registrations were illustrated in a graph, but didn't cause any feedback messages to the patient.

For the possible adverse events for Zoloft according to the set of functions, the following message was shown to the patient if he/she had fulfilled level one; "You seem to have . . . [the actual symptom] and should contact your responsible doctor and tell him/her about your situation and how you feel." If the patient fulfilled level two, the following message was shown: "You seem to have . . . [the actual symptom] and should promptly contact your responsible doctor and tell him/her about your situation and how you feel, if you haven't already done it."

For the possible adverse event for Metformin according to the set of functions, a corresponding message was shown to the patient if he/she fulfilled level one; "You seem to have had problem with your diabetes and should contact your responsible doctor and tell him/her about your situation and how you feel." If the patient registered on level two, the following message was shown: "You seem to have had severe problems with your diabetes and should promptly contact your responsible doctor and tell him/her about your situation and how you feel."

For the possible adverse events for Januvia according to the set of functions, the following message was shown to the patient if he/she had fulfilled the criteria for level one; "You seem to have . . . [the actual symptoms] and should contact your responsible doctor and tell him/her about your situation and how you feel." If the patient had fulfilled the criteria for level two, the following message was shown: "You seem to have . . . [the actual symptoms] and should promptly contact your responsible doctor and tell him/her about your situation and how you feel, if you haven't already done it."

For the possible side effect for Metformin according to the set of functions, a corresponding message was shown to the patient; "You seem to have had a side effect and should contact your responsible doctor and tell him/her about your situation and how you feel."

Test Result Combination Product Zoloft, Metformin and Januvia

Baseline value before test; HbA1c: 51 mmol/mol and Weight: 90 kg

End value after test; HbA1c: 43 mmol/mol and Weight: 85 kg

During the actual period of time of using the combination product based upon Zoloft, Metformin, Januvia and specifically adapted QFM:s and QAFM with a dependent software application, the patient decreased 8 mmol/mol in HbA1c implying a decrease of 16%. The actual dose of Zoloft and Metformin was changed once during the period, starting at respectively 50 mg and 2000 mg, and ending on 25 mg and 1500 mg. The actual dose of Januvia was not changed during the period.

During the test period when the patient was only taking Zoloft and Metformin, i.e. full combination product was not used since the patient did not use the software application and neither took Januvia, the HbA1c slightly rose 5% and the weight was stable.

The invention claimed is:

1. A method of treating a medical condition in a subject, comprising administering to the subject a combination of N substances, wherein N>1, with pharmaceutical activity against said medical condition in combination with a computer program product comprising instructions causing a computer to perform the following steps:
providing a patient with a set of questions according to a question schedule, wherein said set of questions is adapted to said combination of substances and wherein said set of questions serves to identify a possible development of an upcoming side effect;
providing a patient with N sets of questions according to N question schedules, wherein each set of questions is adapted to one of the substances in said combination and wherein each set of questions serves to identify a possible development of an upcoming side effect;
collecting answers to said sets of questions from said patient;
subjecting the answers to said set of questions adapted to said combination of substances to a set of functions, thereby generating a first patient specific feedback information;
subjecting the answers to said sets of questions, each adapted for one of the substances in said combination, to N sets of functions, each adapted for one of the sets of questions, thereby generating second patient specific feedback information;

providing said first and second patient specific feedback to the patient, wherein at least one of said first and second patient specific feedback is directed to making the patient aware of development of a possible upcoming side effect; and optionally extracting information from said answers and providing said information to a database adapted for collecting information during clinical use of said combination of substances.

2. The method according to claim 1, wherein the computer program product comprises instructions causing a computer to perform the following steps:
   providing at least one further respondent in addition to said patient with a second set of questions according to a second question schedule, wherein said second set of questions is adapted to the combination of substances and/or to at least one of the substances in said combination;
   collecting answers to said questions from said further respondent;
   subjecting said answers from said further respondent to a second set of functions adapted to the second set of questions and the combination of substances and/or to at least one of the substances in said combination thereby generating patient-specific feedback information;
   providing said feedback information to the patient and, optionally, to the further respondent; and
   optionally extracting information from said answers from said further respondent and providing said information to a database adapted for collecting information during clinical use of said combination of substances.

3. The method according to claim 1, wherein the computer program product comprising instructions causes a computer to perform a method comprising the steps
   a) providing a patient and optionally a further respondent with sets of questions according to a question schedule, wherein said sets of questions are adapted to the combination of substances and/or to at least one of the substances in said combination;
   b) collecting answers to said questions from said patient and optionally said further respondent;
   c) subjecting said answers to a set of functions adapted for the sets of questions and the pharmaceutical product thereby generating patient-specific feedback information;
   d) providing said feedback information to the patient and optionally to the further respondent;
   e) extracting information from said answers and providing said information to a database adapted for storing information collected during clinical use of said combination of substances;
   f) providing information stored in said database to a reviser subjecting the sets of questions and/or the sets of functions to a revision based on said information stored in said database;
   g) obtaining a revised set of questions and/or a revised set of functions from said reviser; and
   h) repeating steps a)-g).

4. The method according to claim 1, wherein said database adapted for storing information collected from more than one patient, preferably at least 50%, such as at least 75% or substantially 00% of patients, clinically using said combination of substances in combination with said computer program product.

5. The method according to claim 3, wherein said revision is based on information collected from said patient and/or other patients clinically using said combination of substances in combination with said computer program product.

6. The method according to claim 1, wherein said revision is based on information obtained during clinical trials of the substance and/or commercial use of the substance.

7. The method according to claim 1, wherein said database is adapted to store information comprising one or more of: patient identifier, respondent identifier, individual caregiver identifier, organizational caregiver identifier, substance identifier, substance combination identifier, respondent answers, type and date of occurrence of adverse events, type and degree of adverse effects of one or more substance or substance combination, probability of an adverse event, probability of an adverse effect, patient health status, patient history, patient family history, patient genetic information, prescribed dosage or administration regimen, drug-drug interactions, life-style factors.

8. The method according to claim 1, wherein the clinical relevance of the combination of said set of questions and said set of functions has been validated in clinical trials.

9. The method according to claim 1, wherein said set of questions and said set of functions are further related to patient compliance to a preferred or prescribed dosage and/or administration regimen of said combination of substances.

10. The method according to claim 1, wherein said set of questions and said set of functions are further related to an indication of possible occurrence or development of an adverse event.

11. The method according to claim 1, wherein said set of questions and said set of functions are further related to the patient's quality of life.

12. The method according to claim 1, wherein at least a subset of the set of questions is related to the actual administration; actual dosage; perceived and/or measured therapeutic effects; test results and/or perceived quality of life.

13. The method according to claim 1, wherein the method further comprises subjecting said answers to a set of functions specific for the set of questions and the pharmaceutical product thereby generating an updated question schedule, wherein said set of functions optionally use Computer Adaptive Testing and/or Item Response Theory.

14. The method according to claim 1, wherein said set of functions include functions selected from the group consisting of: calculations of target parameters and trend lines; prediction of development of a condition; rules and thresholds for defining when to give notifications.

15. The method according to claim 1, wherein said computer program product comprises instructions causing a computer to provide feedback selected from graphs, diagrams, graphical illustrations and text messages.

16. The method according to claim 1, wherein said method provides feedback only to the patient, or to the patient and to other individuals.

17. A kit of parts comprising a combination of N substances, wherein N>1, with pharmaceutical activity against at least one medical condition, and
   a computer program product comprising instructions causing a computer to perform the following steps:
   providing a patient with a set of questions according to a question schedule, wherein said set of questions is adapted to said combination of substances and wherein said set of questions serves to identify a possible development of an upcoming side effect;
   providing a patient with N sets of questions according to N question schedules, wherein each set of questions is adapted to one of the substances in said combination and wherein each set of questions serves to identify a possible development of an upcoming side effect;

collecting answers to said sets of questions from said patient;

subjecting the answers to said set of questions adapted to said combination of substances to a set of functions, thereby generating a first patient specific feedback information;

subjecting the answers to said sets of questions, each adapted for one of the substances in said combination, to N sets of functions, each adapted for one of the sets of questions, thereby generating a second patient specific feedback information; and providing said first and second patient specific feedback to the patient wherein at least one of said first and second patient specific feedback is directed to making the patient aware of development of a possible upcoming side effect, wherein said computer program product is provided on a physical medium or by means or instructions for accessing and installing the computer program product on a computer.

18. The kit of parts according to claim 17, wherein said computer program product is provided by means or instructions for accessing and installing the computer program product on a computer and said kit further comprises an identifier unique to the kit.

19. The method according to claim 1, wherein the substances in said combination of substances are selected from the group consisting of Aripiprazol (Abilify), Rimonabant (Acomplia), Pioglitazon (Actos), glucoseamine (Glucosine), Octocog alfa (Advate, Advair), Flutikason in combination with Salmeterol (Seretide), zolpidem (Ambien, Stilnox), Insulin glulisin (Apidra), Donepezil (Aricept), irbesartan (Avapro, Aprovel), rosiglitazone (Avandia), metformin in combination with rosiglitazone (Avandamet), glimepiride in combination with rosiglitazone (Avandaryl), bevacizumab (Avastin), Interferon beta (Avonex), Darbepoetin alfa (Aranesp), anastrozole (Arimidex), Kandesartan (Atacand), olmesartan (Benicar, Olmetec), Interferon beta-lb (Betaseron), Interferon beta (Betaferon), exenatide (Byetta), Bikalutamid (Casodex), Celecoxib (Celebrex, Celebra), Escitalopram (Cipralex/Lexapro), duloxetine (Cymbalta), Vareniklin (Champix), Glatiramer (Copaxone), Carvedilol (Coreg), Losartan (Cozaar), Rosuvastatin (Crestor), Ramipril (Tritace), Valsartan (Diovan), Venlafaxin (Efexor), oxaliplatin (Eloxatin), Etanercept (Enbrel), raloxifene (Evista), ezetimibe (Ezetrol, Zetia), Tamsulosin (Flomax, Flomaxtra, Urimax), fluticasone (Flovent, Flixotide), Alendronic acid (Fosamax), Gemcitabine (Gemzar), imatinib mesylate (Gleevec, Glivec), Trastuzumab (Herceptin), insulin lispro (Humalog), Adaiimumab (Humira), Lopinavir/ritonavir (Kaletra), Sumatriptan (Imitrex, Imigran), Sitagliptin (Januvia), insulin glargin (Lantus), Fenofibrate (Lipanthyl, TriCor), atorvastatin (Lipitor), Insulin Detemir (Levemir), amlodipine and benazepril (Lotrel), Leuprorelin, (Lupron, Leuplin), pregabalin (Lyrica), rituximab (Mabthera, Rituxan), Telmisartan (Micardis), Esomeprazole (Nexium), amlodipine (Norvasc), insulin aspart (NovoLog, NovoMix, NovoRapid), repaglinid (NovoNorm), Rabeprazole (Pariet), paroxetine (Paxil, Seroxat), Pantoprazole (Protonix, Pantozol, Pantoloc), Clopidogrel (Plavix), pravastatin (Pravachol), Epoetin Alfa (Procrit, Eprex), takrolimus (Protopic), budesonid (Pulmicort), interferon beta-1 a (Rebif), sibutramin (Reductil), Infliximab (Remicade), Risperidon (Risperdal), Metoprolol (Seloken, Toprol), quetiapine (Seroquel), Tiotropium (Spiriva), budesonide and formoterol (Symbicort), Montelukast (Singulair), Docetaxel (Taxotere), Topiramat (Topamax), Emtricitabin and Tenofovirdisoproxil (Truvada), ezetimibe and simvastatin (Vytorin), bupropion (Wellbutrin), Betametason in combination with Kalcipotriol (Xamiol) calcipotriene (Taclonex), simvastatin (Zocor), Sertralin (Zoloft), zoledronic acid (Zometa), Olanzapin (Zyprexa), cetirizine (Zyrtec), and ticagrelor (Brilique).

* * * * *